United States Patent [19]
Zuckerman

[11] Patent Number: 5,495,850
[45] Date of Patent: Mar. 5, 1996

[54] METHOD FOR THE MEASUREMENT OF OXYGEN CONCENTRATION LEVELS BY THE STEADY-STATE DETERMINATION OF FLUORESCENCE LIFETIME

[76] Inventor: Ralph Zuckerman, 226 W. Rittenhouse Sq., Philadelphia, Pa. 19103

[21] Appl. No.: 378,147

[22] Filed: Jan. 25, 1995

Related U.S. Application Data

[62] Division of Ser. No. 231,191, Apr. 21, 1994.

[51] Int. Cl.$^6$ ........................................ A61B 5/00
[52] U.S. Cl. ................................ 128/634; 356/41
[58] Field of Search ................................ 128/633, 634, 128/665; 250/461.1; 356/41

[56] References Cited

U.S. PATENT DOCUMENTS

| | | | |
|---|---|---|---|
| 4,115,699 | 9/1978 | Mizuta et al. | 250/461 |
| 4,476,870 | 10/1984 | Peterson et al. . | |
| 4,579,430 | 4/1986 | Bille . | |
| 4,810,655 | 3/1989 | Khalil et al. . | |
| 4,947,850 | 8/1990 | Vanderkooi et al. . | |
| 5,039,219 | 8/1991 | James et al. . | |
| 5,120,510 | 6/1992 | Gourley et al. | 128/634 |
| 5,186,173 | 2/1993 | Zuckerman . | |
| 5,251,633 | 10/1993 | Wunderling et al. | 128/634 |
| 5,281,825 | 1/1994 | Berndt et al. . | |
| 5,317,162 | 5/1994 | Pinsky et al. . | |
| 5,318,023 | 6/1994 | Vari et al. | 128/633 |
| 5,341,805 | 8/1994 | Stavridi et al. | 128/633 |
| 5,383,452 | 1/1995 | Buchert | 128/633 |

OTHER PUBLICATIONS de Coo, F. A., Zonnenberg, B. A., and Trap, N. H., "Prolonged Normothermic Perfusion of the Isolated Bovine Eye: Initial Results", Curr. Eye Res., 12 (4):293–301 (Apr. 1993).
Vanderkooi, J. et al., "An Optical Method for Measurement of Dioxygen Concentration Based Upon Quenching of Phosporscence", J. Biol., Chem. 262(12); 5476–5482 (Apr. 1987).

Primary Examiner—Angela D. Sykes
Assistant Examiner—Eric F. Winakur
Attorney, Agent, or Firm—William H. Eilberg

[57] ABSTRACT

Methods are described for the in vivo topographic determination of tissue and bodily fluid oxygen concentration or $PO_2$ within an imaged tissue, as well as a method for measuring blood or bodily fluid $PO_2$ with a fiber optic catheter. In the first method, a lipid soluble, biocompatible fluorescent probe substance is administered to an animal body and accumulates within the lipid bilayers of its tissue cells. In the second method, the fluorescent probe substance is conjugated to a large molecular mass protein which causes it to be retained within a bodily fluid such as blood. In the third method describing a catheter design, in which $PO_2$ is measured at the catheter tip, the tip contains the fluorescent probe substance dissolved in a viscous nonpolar solvent. In all methods described, a fluorescent probe substance is preferred whose fluorescence lifetime is quenched by molecular oxygen, and oxygen concentration or $PO_2$ is determined by measuring the fluorescence anisotropy of the fluorescent probe substance. The bodily fluid or tissue containing the biocompatible fluorescent probe substance, or the fluorescent probe substance in a nonpolar solvent within a catheter tip, is irradiated with continuous linearly polarized ultraviolet light at a wavelength strongly absorbed by the fluorophore. The emitted fluorescence is resolved into its vector components parallel and perpendicular to the plane of polarization of the excitation light, thereby permitting the calculation of the fluorescence anisotropy of the irradiated specimen. Tissue and/or bodily fluid $PO_2$ of the imaged specimen, or the $PO_2$ of a fluid at the tip of a sealed catheter, is determined by applying a mathematical function which relates the fluorescence anisotropy of an $O_2$-quenchable fluorophore to oxygen concentration or partial pressure.

15 Claims, 6 Drawing Sheets

METHOD FOR THE MEASUREMENT OF OXYGEN CONCENTRATION LEVELS BY THE STEADY-STATE DETERMINATION OF FLUORESCENCE LIFETIME

RELATED APPLICATIONS

This application is a divisional application of application Ser. No. 08/231,191, filed Apr. 21, 1994, entitled Method and Apparatus for the In Vivo Measurement of Oxygen Concentration Levels By the Indirect Determination of Fluorescence Lifetime, the entire disclosure of which is incorporated by reference herein.

BACKGROUND OF THE INVENTION

Molecular oxygen is a critical requirement for cellular function in animals, while the protection from $O_2$ is required for the function of plant enzymes such as the nitrogenases. Animals, and mammals in particular, are critically dependent upon the continuous supply and utilization of $O_2$ in the processes which maintain life. This is particularly true for high $O_2$-consuming tissues such as neural tissues and muscle, both striated and smooth. Interruption of oxygen delivery to these tissues, for times as brief as minutes, can result in cell death and loss of functions critical to organ function. Moreover, it is the oxygen concentration within tissues, rather than within blood or other bodily fluids, which ultimately supports cellular function. Therefore, the measurement of bodily fluid and tissue oxygen concentrations is of pivotal importance to clinical medicine, with the compromise of oxygen delivery to tissues occurring in a host of vascular diseases, such as arteriosclerosis, diabetes, sickle cell disease, and impaired wound healing to name a few. It is therefore not surprising that numerous patents have been issued for methods and devices which measure blood and bodily fluid oxygen concentration, and this inventor's U.S. Pat. No. 5,186,173 (hereinafter the Zuckerman '173 patent) for the first measurement of tissue oxygen concentration in vivo.

These patents, although each addressing problems involved in the noninvasive determination of bodily fluid or tissue $PO_2$, suffer from deficiencies which have precluded their widespread application in clinical medicine. To achieve the requirement of noninvasive measurement recent patents have turned to optical methods, which involve the quenching of phosphorescence or fluorescence of a dye by dioxygen. For example, patents such as that of U.S. Pat. No. 4,476,870 (Peterson et. al.) have developed catheter designs in which a fluorescent substance, such as perylene, is housed within a sealed catheter which may be inserted into blood vessels and its fluorescence quenching by $O_2$ in blood measured by use of fiber optics. This device, although providing the ability to measure bodily fluid or blood $PO_2$, suffers from two deficiencies. First, the $PO_2$ of blood may be measured accurately only after the catheter probe is externally calibrated prior to its insertion into a blood vessel; and second, the technique provides no topographic information, as $PO_2$ is measured at a single locus, viz., at the probe tip. In U.S. Pat. No. 4,810,655, Khalil et. al. purport to overcome the need for prior calibration of the catheter before its every usage by measuring phosphorescence lifetime instead of intensity. Although in theory a direct lifetime system should overcome the need for prior calibration, in practice, as shown in Table 4 of the Khalil et. al. patent, the phosphorescence lifetimes of the porphyrins employed change with light exposure, making calibration prior to use still necessary. In addition, the time-resolved direct lifetime system would be cumbersome to implement, and less precise than a steady-state approach. Vanderkooi and Wilson (U.S. Pat. No. 4,947,850) developed a procedure based upon the determination of the phosphorescence lifetime of an $O_2$-sensitive probe substance, such as a metallo-porphyrin bound tightly to albumin, which phosphoresces on a timescale of fractions of a millisecond ($10^{-3}$ sec), and whose phosphorescence lifetime is reduced (quenched) by dioxygen. Here the $O_2$-sensitive probe is a phosphorescing molecule which may be injected into the blood stream, thereby permitting topographic determination of the $PO_2$ of blood within the vasculature of an imaged tissue. However, due to self-quenching of the metallo-porphyrins, as well as the other probes described by Vanderkooi, these probe molecules cannot be used alone. That is, self-quenching results in probe concentration dependent changes in decay time which are greater than those induced by molecular oxygen. Since it is impossible to know the precise probe concentration in the blood, due to leakage at the injection site and variations in blood volume in different animals or humans, they must modify the probe to eliminate self-quenching. As stated in U.S. Pat. No. 4,947,850 (col. 3, line 15) "porphyrins are preferably employed and said compositions are preferably admixed with proteinaceous compositions which bind with the phosphorescent composition . . . Albuminous . . . compositions are preferred." As described in their publication Vanderkooi, J. et. al., "An Optical Method for Measurement of Dioxygen Concentration Based Upon Quenching of Phosphorescence", *J. Biol. Chem.*, 262(12): 5476–5482 (April 1987), the technique will simply not work without albumin or some other large molecular mass protein bound to the probe molecule. When injected intravenously into the blood the large molecular mass protein (M.W.=67,000) prevents the probe molecule from passing through the small junctions or lipid membranes of the blood vessel wall, and thereby limits the measurement to oxygen concentration in the blood. Similarly, U.S. Pat. No. 4,579,430 (Bille) discloses an invention that allows the determination of oxygen saturation, percentage binding of $O_2$ to blood hemoglobin, within retinal vessels. In a host of diseases the oxygen saturation and oxygen concentration of the blood, as revealed by previous patents, remains normal although the tissue is believed to become hypoxic. Such diseases include diabetes, retinopathy of prematurity, and hypertensive and arteriosclerotic diseases. Similarly, during long surgeries, such as bypass surgery, carotid artery surgery and during prolonged intensive care, the oxygen saturation and/or concentration of the blood is carefully monitored and maintained, yet moderate to severe brain damage due to hypoxia has been known to occur. It is the oxygen concentration within tissues which is relevant to its functioning and health, and tissue oxygen concentration depends upon tissue oxygen consumption rate, blood velocity, and vessel caliber, in addition to blood oxygen concentration or saturation. Therefore, it is of paramount importance to be able to measure the $PO_2$ of tissue in space and time.

The noninvasive, topographic measurement of tissue $PO_2$ was addressed in the the Zuckerman '173 patent. In this patent, a highly lipid soluble probe substance, such as sodium pyrenebutyrate, is injected intravenously or intraperitoneally, or applied topically when appropriate. The lipid soluble, biocompatible probe substance leaves the blood and accumulates within the lipid bilayers of tissue cells. Here the probe is essentially the tissue itself, once pyrenebutyrate accumulates within the lipid bilayers of its cells. This and the digital imaging system detailed within the patent allows the first topographic determination of tissue oxygen concentration, which supports tissue health and function. The concentration of $O_2$ is determined in the Zuckerman '173 patent by the measurement of fluorescence intensity, according to the Stern-Volmer equation, written in terms of fluorescence intensities. The invention of the Zuckerman '173 patent, although allowing the first noninvasive determination of tissue $PO_2$ in space and time, suffers from two deficiencies which preclude its clinical application, and which presently limits its utility to research applications on laboratory animals. The most significant limitation results from the fact that fluorescence intensity is determined by both the concentration of pyrenebutyrate in space within tissues, which varies due to spatial differences in lipid composition of the cells within tissues, as well as by the spatial distribution of tissue oxygen concentration. To circumvent this problem, and to extract the oxygen concentrations at a plurality of locations, the fluorescence intensity at each locus is ratioed against the fluorescence intensity of the same location when the tissue is brought to a $PO_2$ of 0 mm Hg (in the absence of oxygen). This may be accomplished by breathing the animal on 100% $N_2$ at the end of the experiment. Such a procedure cannot be applied clinically on humans as it would undoubtedly result in cell death, evidenced in brain damage or death. The second deficiency in the invention of the Zuckerman '173 patent resides in the optical filtering effects of blood on the fluorescence intensities at the emission wavelength of pyrenebutyrate. This may similarly be corrected in a laboratory situation by the separate measurement of the optical density of blood within the vasculature of the imaged tissue.

Both of the deficiencies in the device and method of the Zuckerman '173 patent may be obviated by the direct measurement of fluorescence lifetime (decay) instead of fluorescence intensity. Measurement of fluorescence lifetime at a given $PO_2$ and within a given tissue, once determined in a laboratory calibration of the instrument, would obviate the need to bring the tissue to a $PO_2$ of 0 mm Hg in the clinic, as the fluorescence decay constant is independent of pyrenebutyrate concentration, and is similarly unaffected by the absorbance of blood within the vasculature. However, fluorescence lifetime occurs on the timescale of nanoseconds ($10^{-9}$ see), and in addition to the cumbersome and expensive apparatus required directly to measure such short fluorescence lifetimes at a plurality of locations, would require intense pulsed laser excitation (pulse duration <20 nanoseconds) of the tissue at the ultraviolet excitation wavelength to achieve usable signal-to-noise ratios. Since the quantum efficiency of pyrenebutyrate and other fluorescent probe molecules is generally less than 0.5, photon absorption which is not converted into emitted radiation by fluorescence would be converted to heat, thereby causing tissue damage. Tissue damage subsequent to an intense laser pulse, used in a time-resolved direct fluorescence lifetime determination, is the major drawback to the use of this approach in vivo. Herein resides the need for a method for the topographic measurement of oxygen concentration in vivo by a steady-state, rather than time-resolved, procedure which provides an indirect determination of fluorescence lifetime.

In view of the deficiencies of the prior art, it would be desirable to have a method which can be applied in numerous forms and which allows the determination of bodily fluid, blood, and tissue $PO_2$ in space and time by an indirect determination of fluorescence lifetime. Such a method would allow the construction of an $O_2$-sensitive catheter, which may be inserted into a blood vessel, and which does not require cumbersome external calibration prior to its every usage. Similarly, such a method would, by intravenous injection of a biocompatible lipid soluble fluorescent dye, and by the application of digital image processing techniques, allow the topographic determination of tissue $PO_2$, as well as the determination of blood $PO_2$ within the vasculature of the imaged tissue. By extension, the application of optical serial sectioning methodologies would allow the first determinations of tissue and blood $PO_2$ distributions in three dimensions, tomographically within a volume of imaged tissue. Most importantly, such a procedure would be eminently suitable for clinical applications involving diagnosis and treatment of vascular, metabolic and other diseases in humans.

OBJECTS OF THE INVENTION

Accordingly, it is a general object of this invention to provide a method and apparatus for the in vivo topographic determination of tissue and bodily fluid oxygen concentration or $PO_2$ within an imaged tissue, as well as a method and apparatus for measuring blood or bodily fluid $PO_2$ with a fiber optic catheter which overcomes the disadvantages of the prior art.

It is a further object of this invention to provide an in vivo method and apparatus for determining tissue and bodily fluid oxygen concentration using a fluorescent probe substance whose fluorescence lifetime is quenched by molecular oxygen, and oxygen concentration or $PO_2$ is determined by measuring the fluorescence anisotropy of the fluorescent probe substance.

It is another object of this invention to provide an in vivo method and apparatus for determining tissue and bodily fluid oxygen concentration which is accurate, non-intrusive and provides reproducible results.

SUMMARY OF THE INVENTION

These and other objects of this invention are achieved by providing an apparatus and methods for the in vivo topographic determination of tissue and bodily fluid oxygen concentration or $PO_2$ within an imaged tissue, as well as a method for measuring blood or bodily fluid $PO_2$ with a fiber optic catheter. In the first method, a lipid soluble, biocompatible fluorescent probe substance is administered to an animal body and accumulates within the lipid bilayers of its tissue cells. In the second method, the fluorescent probe substance is conjugated to a large molecular mass protein which causes it to be retained within a bodily fluid such as blood. In the third method describing a catheter design, in which $PO_2$ is measured at the catheter tip, the tip contains the fluorescent probe substance dissolved in a viscous nonpolar solvent. In all methods described, a fluorescent probe substance is preferred whose fluorescence lifetime is quenched by molecular oxygen, and oxygen concentration or $PO_2$ is determined by measuring the fluorescence anisotropy of the fluorescent probe substance. The bodily fluid or tissue containing the biocompatible fluorescent probe substance, or the fluorescent probe substance in a nonpolar solvent within a catheter tip, is irradiated with continuous linearly polarized ultraviolet light at a wavelength strongly absorbed by the fluorophore. The emitted fluorescence is resolved into its vector components parallel and perpendicular to the plane of polarization of the excitation light, thereby permitting the calculation of the fluorescence anisotropy of the irradiated specimen. Tissue and/or bodily fluid $PO_2$ of the imaged specimen, or the $PO_2$ of a fluid at the tip of a sealed catheter, is determined by applying a mathematical function which relates the fluorescence anisotropy of an $O_2$-quenchable fluorophore to oxygen concentration or partial pressure.

BRIEF DESCRIPTION OF THE DRAWINGS

Other objects and many attendant features of this invention will become readily appreciated as the same becomes better understood by reference to the following detailed description when considered in connection with the accompanying drawings wherein.

Figure 1:
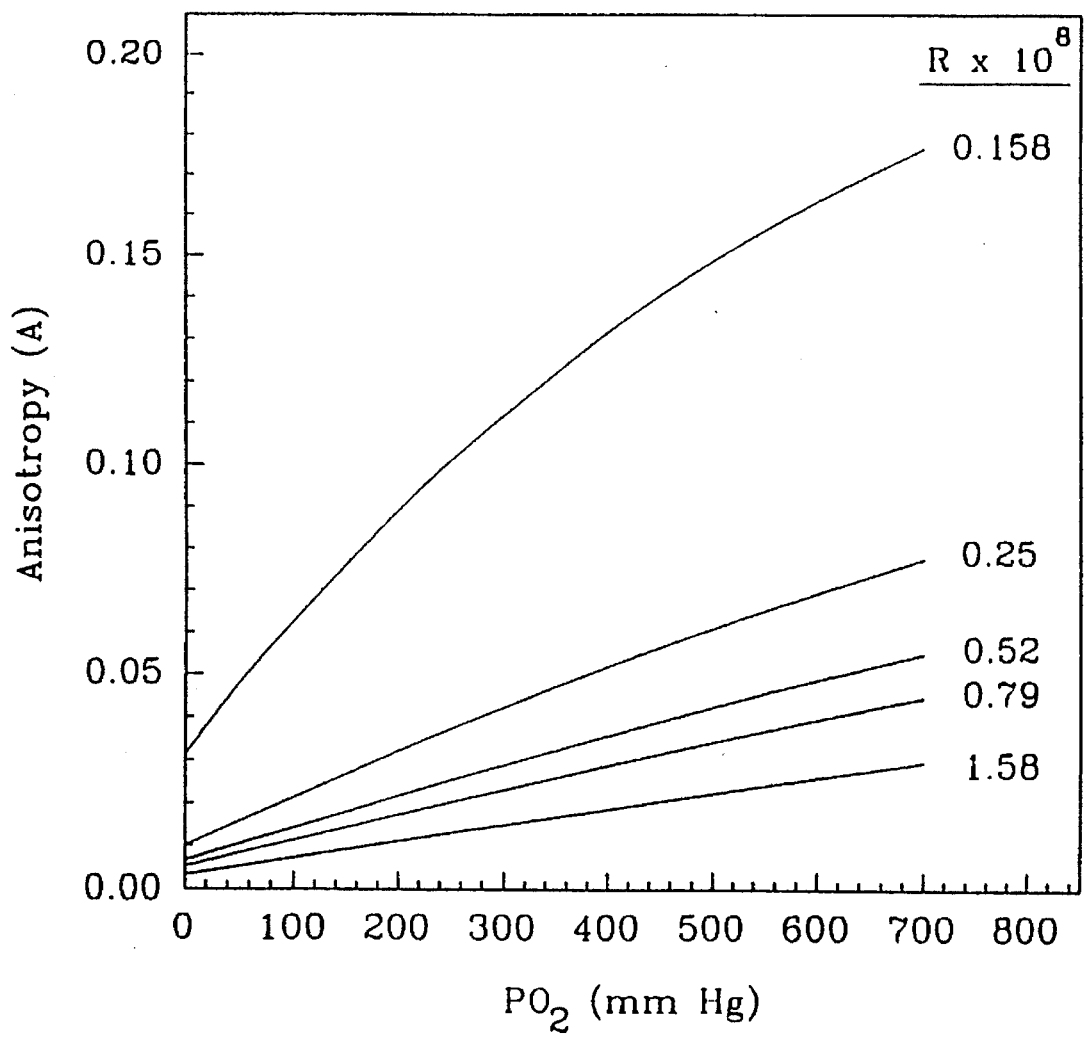
FIG. 1 is a theoretical plot of the fluorescence anisotropy of an $O_2$-quenchable fluorophore dissolved in a nonpolar solvent as a function of the oxygen partial pressure ($PO_2$) of the fluorophore-containing solution. A family of curves is derived from equation 6 for the range of Brownian rotational motions (R) known to occur in the lipids of living tissue cells. Fluorescence anisotropy increases monotonically with increasing $PO_2$ at all rotational rates.

Exhibit A is the source code excerpted from "Software for the Acquisition, Manipulation and Analysis of Video Images", Copyright 1993, Biometric Imaging, Inc.

DETAILED DESCRIPTION OF PREFERRED EMBODIMENTS

The present invention addresses several problems inherent in the prior art. The invention is based upon the well-accepted physical principle that absorption and emission of photons by fluorophores occur via electric dipole transition moments which have well-defined orientations within the molecular frame of the fluorophore. In a nonpolar solvent or lipid bilayer containing randomly oriented fluorophores only suitably oriented molecules can be excited by linearly polarized light, thus creating a nonequilibrium orientation of excited and fluorescing molecules. This anisotropy, and its rotational relaxation, are reflected in the polarization of the emitted light. The case of time-resolved fluorescence anisotropy induced by a pulse of linearly polarized light may be described by the following equation:

$$A(t) = A_o e^{-6\bar{R}t} \tag{1}$$

where A is fluorescence anisotropy, t is time of observation after pulsed excitation, $\bar{R}$ is mean molecular rotation time in radians/sec, and $A_o$ is the fluorescence anisotropy in the "frozen" state, in the absence of Brownian rotation. However, if fluorescence anisotropy is measured with steady-state, continuous excitation, A is an average of the time-resolved decay over time weighted by the decay of intensity:

$$A(\tau) = \frac{\int_o^\infty e^{-t/\tau} A(t) dt}{\int_o^\infty e^{-t/\tau} dt} = \frac{1}{\tau} \int_o^\infty e^{-t/\tau} A(t) dt \tag{2}$$

where $\tau$ is the fluorescence lifetime of the fluorophore.

Carrying out the transform results in the Perrin equation:

$$A = \frac{A_o}{1 + 6\bar{R}\tau} \text{ or } \frac{A_o}{A} = 1 + 6\bar{R}\tau \tag{3}$$

which for an ideal spherical molecule becomes:

$$\frac{A_o}{A} = \frac{1 + R_g T}{\eta V} \tau \tag{4}$$

where $R_g$ is the gas constant, T is temperature, $\eta$ is viscosity, and V is the fluorophore's hydrodynamic volume.

The present invention considers, for the first time, the case of an $O_2$-quenched fluorophore, such as sodium pyrenebutyrate, accumulated within a nonpolar solvent or lipid bilayer, such as those found in all tissue cells in the body. The fluorescence lifetime of the fluorophore may be related respectively to oxygen concentration or partial pressure by the following forms of the Stern-Volmer relation:

$$\tau = \frac{\tau_o}{1 + K_D[O_2]} \text{ or } \frac{\tau_o}{1 + \alpha K_D PO_2} \tag{5}$$

where $\alpha$ is the Bunsen solubility coefficient, $K_D$ is the dynamic quench constant, and $\tau_o$ is fluorescence lifetime in the absence of $O_2$. By combining equations 3 and 5, we derive a mathematical relationship which formally relates oxygen partial pressure to steady-state fluorescence anisotropy:

$$PO_2 = \frac{A_o - A(6\bar{R}\tau_o + 1)}{\alpha K_D (A - A_o)} \tag{6}$$

Equation 6, therefore, is the central and novel concept of the present invention, and demonstrates that steady-state fluorescence anisotropy measurements may be used as a precise procedure, which may be implemented in simple configurations, to determine (i) the $PO_2$ of tissues in space and time subsequent to the accumulation of an $O_2$-quenchable fluorophore within the lipid bilayers of its tissue cells, (ii) the topographic distribution of blood $PO_2$, subsequent to the accumulation of the fluorophore within the lipid bilayers of red blood cells, or for a fluorophore conjugated to a protein injected into the blood stream and (iii) the $PO_2$ at the tip of an insertable catheter whose tip contains a fluorophore such as pyrene in a nonpolar solvent or lipid such as mineral or paraffin oils, separated from the sample by an $O_2$-permeable membrane.

The mathematical relation expressed in equation 6 is plotted in FIG. 1 for the range of Brownian rotational motions known to occur in the lipids of tissue cells. As shown in FIG. 1, steady-state fluorescence anisotropy increases in a systematic way with increasing values of $PO_2$ at all rotational rates. In other words, as $PO_2$ is raised the fluorescence lifetime of the fluorophore is shortened (equation 5), thereby reducing the angle swept out by the fluorophore during its lifetime. Fluorescence anisotropy, therefore, increases with increasing $PO_2$. The other variables which would affect fluorescence anisotropy in such a situation, in addition to $PO_2$, are temperature and viscosity of the lipid bilayer. However, it is well known that in the case of an imaged tissue and/or vasculature in vivo, the body superbly regulates these variables. Similarly, a catheter with an $O_2$-sensitive tip of small volume will quickly come into equilibrium with the temperature of the blood within a blood vessel into which it is inserted. Moreover, as demonstrated in equation 4, small variations in body or catheter tip temperature encountered in some disease states may be compensated for precisely by concomitant temperature measurement and the application of this equation to the calculation of $PO_2$ from steady-state fluorescence anisotropy measurements.

The present invention has all of the advantages of a direct fluorescence lifetime system, without the need for intense, pulsed laser excitation and its potentially damaging effects on the imaged specimen. In addition, the cumbersome and expensive equipment required to measure fluorescence decays in the 40–135 nanosecond range are avoided. Similarly, since steady-state, continuous fluorescence anisotropy determinations are the time average of a hugh number of fluorescence decay events, such steady-state measurements must be more precise than any time-resolved procedure. The present invention determines $PO_2$ by measurement of steady-state fluorescence anisotropy, while in U.S. Pat. No. 4,476,870 (Peterson) as well as Zuckerman '173 patent, fluorescence intensity is the variable measured. Furthermore, the present invention differs from the invention disclosed in U.S. Pat. No. 4,810,655 (Khalil el. al. ) and that of U.S. Pat. No. 4,947,850 (Vanderkooi) in that both patents determine $PO_2$ from direct measurements of the lifetimes of phosphorescent substances. Phosphorescing substances have much longer, and therefore easier to measure, lifetimes than the preferred fluorescing substances employed in this invention. In the present invention, an indirect measure of fluorescence lifetime, viz. fluorescence anisotropy, is employed in simple-to-implement configurations to provide measurements of tissue and bodily fluid $PO_2$ in vivo, without the limitations of the prior art.

The following figures depict embodiments of the present invention for the topographic measurement of tissue $PO_2$ and the topographic determination of the distribution of blood $PO_2$ within the vasculature of an imaged tissue. In addition, a catheter design, which does not require calibration prior to every usage is also disclosed. It would be readily appreciated by one skilled in the art in view of this disclosure, however, that other specimens, biologic or physical, might be assessed with respect to their oxygen concentration distribution by variations of the designs herein disclosed using the method of the present invention.

As shown below, fluorescence anisotropy is operationally and formally described by the following equation:

$$A = \frac{I_{\|}G - I_{\perp}}{I_{\|}G + 2I_{\perp}} = \frac{A_o(\alpha K_d PO_2 + 1)}{6\bar{R}\tau_o + \alpha K_D PO_2 + 1} \quad (7)$$

where $I_{81}$ and $I_{195}$ are the intensities of fluorescence emission with their electric vectors respectively parallel and perpendicular to that of the linearly polarized exciting radiation, and G is an empirical correction factor used to correct for the dichroic mirror's transmission efficiency in the parallel and perpendicular planes, and where additional symbols used in the formal definition of anisotropy are as described above.

Figure 2:
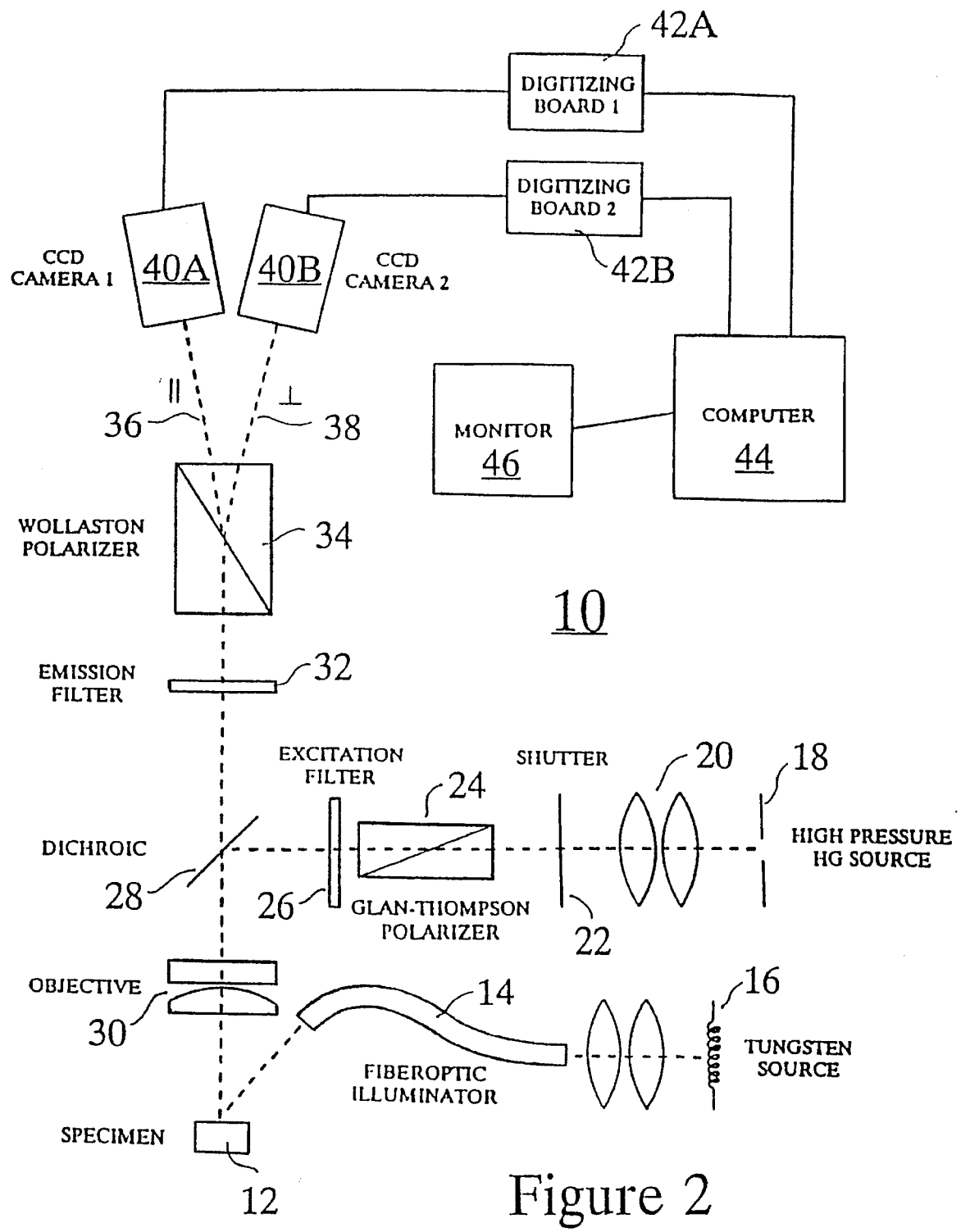
FIG. 2 is a schematic illustration of an imaging apparatus used to determine the topographic distribution of tissue and bodily fluid $PO_2$ within an imaged specimen.

FIG. 2 is a schematic of an apparatus 10 designed for the topographic mapping of tissue and blood $PO_2$ in an imaged tissue. An $O_2$-quenchable, biocompatible probe substance, such as sodium pyrenebutyrate in a suitable solvent or incorporated in liposomes, is injected intravenously into the host organism. The tissue 12 is illuminated with linearly polarized ultraviolet light (UV) by a fiberoptic illuminator 14 utilizing a tungsten source 16. The radiant energy of a high pressure mercury bulb 18 is gathered by a collector lens 20, is shuttered by a shutter 22, and passes through a Glan-Thompson polarizer 24 (Ealing, Inc.). The UV light is spectrally shaped by an excitation filter 26 (340 nm peak, 25 nm half bandpass) and is then reflected by a dichroic mirror 28 (Omega Optical) which reflects wavelengths <400 nm through an objective lens 30 to the imaged tissue. Emitted fluorescence (wavelengths >400 nm) from the excited tissue 12 is gathered by the objective lens 30 and passes through the dichroic mirror 28, and through an emission filter 32, which passes wavelengths from 400–420 nm to a Wollaston prism polarizer 34 which resolves the emitted fluorescence into its linearly polarized components parallel 36 and perpendicular 38 to the plane of excitation polarization. The vector components ($I_{\|}$ and $I_{\perp}$ are respectively and simultaneously detected by the CCD (charge coupled devices) chips of two video cameras 40A and 40B (e.g. Xybion model 250). It is obvious to one skilled in the art that alternative optical detectors with sufficient spatial resolution, such as slow scan chilled CCD cameras, SIT or ISIT tube cameras, or photodiode arrays (not shown) would also be suitable for the detection of the two-dimensional distributions of the parallel and perpendicular components of the emitted fluorescence. The outputs of the two video cameras are digitized by two digitizing boards 42A and 42B (such as sold by Imaging Technologies or under the designation model DT3851 by Data Translation) within a microcomputer 44, (e.g., an IBM® or clone computer, preferably having a processing chip operating at 33 or 66 MHz). Such a device is sufficient for the task and for subsequent image processing prior to display on the monitor 46.

The computer utilizes the software which is produced and copyrighted by Biometric Imaging Inc. The source code for that software is attached hereto and allows the variation of the slopes and offsets at each pixel location within the CCD array to be corrected by a correction file, thereby ensuring uniform responsivity across the detector array. Similarly, the software package allows pixel intensities within the array to be quantified, filtered, averaged, and anisotropy to be calculated at a plurality of locations by means of equation 7 and converted to a two dimensional representation of tissue $PO_2$ by the application of equation 6 at each pixel locus. The present prototype apparatus allows the gathering of more than 300,000 values of tissue $PO_2$ in space within approximately 33 milliseconds. The values for the constants in equation 6 are determined during calibration experiments which involve the simultaneous measurement of tissue $PO_2$ by an oxygen microelectrode and by the indirect lifetime (anisotropy) system.

Should the autofluorescence of the tissue at the emission wavelength show some degree of anisotropy, due to the presence of endogenous fluorophores with short fluorescence lifetimes (<20 nanoseconds), and which are therefore not quenched by physiologic levels of $O_2$, then such "auto-anisotropy" can be imaged and saved to disk prior to the injection of the biocompatible, $O_2$-quenchable fluorescent probe substance. In this case, subsequent to the injection of the $O_2$-quenchable probe substance, the total anisotropy ($A_{total}$) can be related to its component anisotropies "auto-anisotropy" or $A_{tissue}$, and the $O_2$-dependent anisotropy, $A_{probe}$) by the following equation:

$$A_{total} = \frac{a(A_{tissue}) + b(A_{probe})}{a+b} \quad (8)$$

where a+b=1. The $O_2$-dependent anisotropy can then be separated from the total anisotropy by equation 9, where $A(PO_2)$ is the $PO_2$-dependent anisotropy, and a is a constant determined empirically in experiments in which tissue $PO_2$ is measured simultaneously by an $O_2$ microelectrode and by optical measurements of fluorescence anisotropy.

$$A_{probe} \text{ or } A(PO_2) = \frac{A_{total} - a(A_{tissue})}{1-a} \quad (9)$$

This correction can be rapidly and conveniently implemented on a pixel-by-pixel basis by programs within the software package.

An immediate advantage of the present procedure over the invention of the Zuckerman '173 patent, which depends upon the measurement of fluorescence intensities rather than anisotropy, should be evident to those skilled in the art. That is, in that patent, tissue $PO_2$ measurements can only commence after the $O_2$-quenchable fluorescent probe substance has reached equilibrium (stable) concentrations within the imaged tissue since fluorescence intensity in space and time is related to the concentration of probe in the tissue as well as to tissue $PO_2$. In the indirect lifetime system herein depicted, fluorescence anisotropy, which is insensitive to probe concentration, rather than intensity is the determinant of tissue $PO_2$, thereby allowing $PO_2$ measurements to commence as soon as sufficient probe substance has accumulated to provide suitable signal-to-noise levels. Similarly, the anisotropy method is insensitive to the time-dependent degradation of the probe substance by metabolism, thereby permitting tissue $PO_2$ to be determined topographically for extended time periods.

It should be pointed out at this juncture that pseudocoloring programs are contained in the software package of Exhibit A to allow optical maps of tissue $PO_2$ to be depicted in two dimensional space by assigning different hues to different values of tissue $PO_2$, with an accompanying scale which would allow rapid interpretation of the distribution of tissue $PO_2$ by the clinician. The programs written to implement the indirect lifetime system can proceed essentially in "real time", thereby allowing the clinician to view immediately the effects of treatment modalities designed to increase tissue oxygenation (e.g. laser treatment employed to increase retinal tissue $PO_2$ used frequently in the treatment of diabetic retinopathy).

The power of the indirect lifetime system in imaging tissue $PO_2$ can be extended from two to three dimensions by the implementation of optical serial sectioning either by confocal techniques or by the application of digital deconvolution programs, such as those contained in Exhibit A. In this manner a tomographic view of tissue $PO_2$ can be effected, allowing tissue and blood $PO_2$ to be imaged in three dimensions within volumes of tissue. Such three-dimensional information could be conveniently pseudocolored, and by means of three-dimensional reconstruction algorithms, be depicted on the monitor screen. Optical serial sectioning and 3-D reconstruction would allow the clinician to detect and treat abnormal regions of tissue $PO_2$ located at various depths within the imaged tissue.

Figure 3:
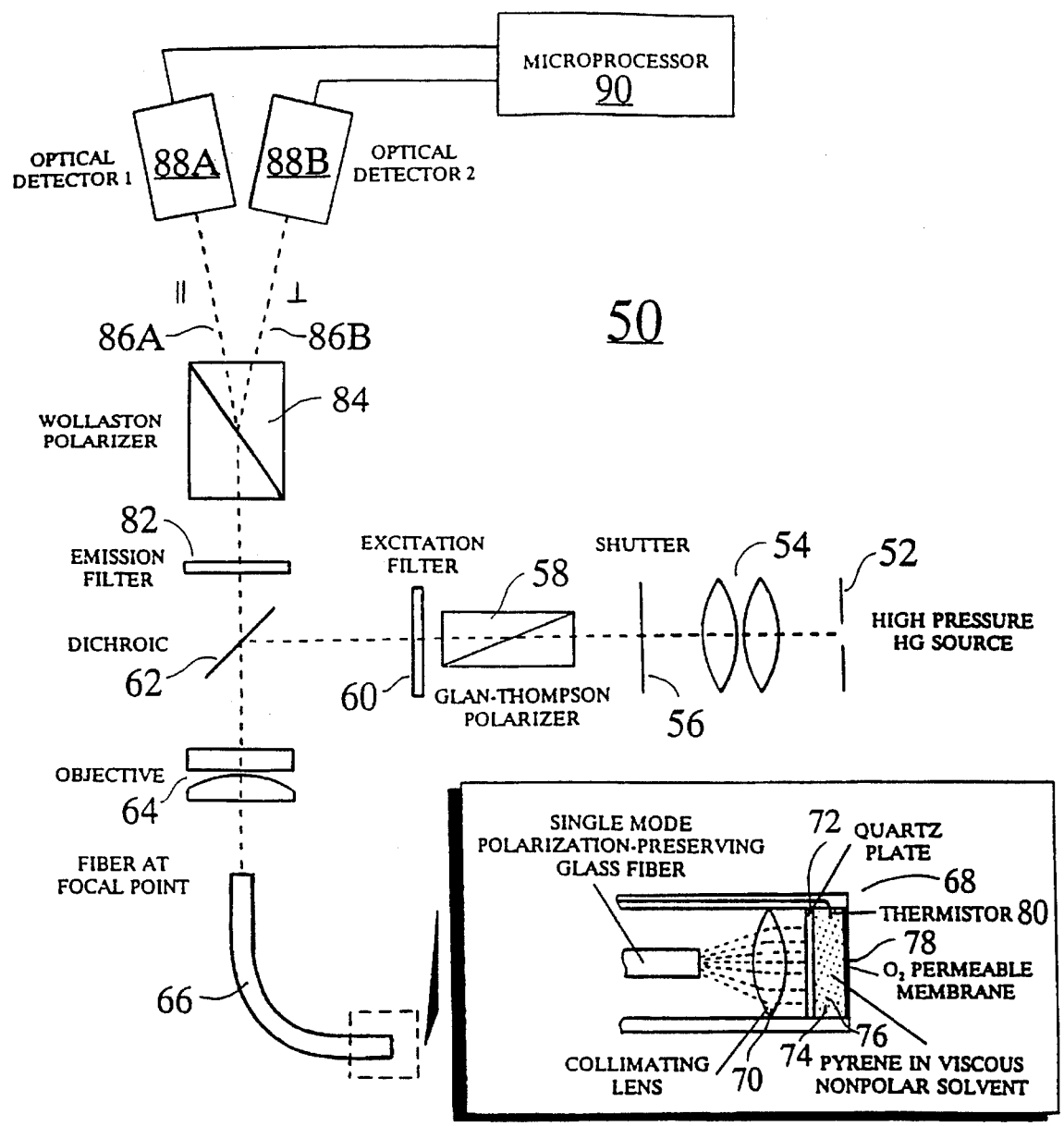
FIG. 3 is an apparatus of the present invention used to measure the oxygen concentration of $PO_2$ of a fluid contacting the tip of a sealed fiber optic catheter.

FIG. 3 shows an apparatus 50 constructed in accordance with the present invention to implement the indirect fluorescence lifetime system in a sealed catheter design which does not require calibration prior to its every usage. As in the previous embodiment the radiant energy of a high pressure mercury bulb 52 is gathered by a collector lens 54, is shuttered via shutter 56, and passes through a Glan-Thompson polarizer 58 (such as sold by Ealing, Inc. under the designation of catalog number 34-5223). The UV light is spectrally shaped by an excitation filter 60 (340 nm peak, 25 nm half bandpass) and is then reflected by a dichroic mirror 62 (such as sold by Omega Optical under the designation 400DCLP) which reflects wavelengths <400 nm through an objective lens 64. A single mode polarization-preserving glass fiber 66 (such as sold by Ealing, Inc., under the designation model HB450) is fixed at the focal point of the objective lens. The core diameter of such fibers is typically <10 microns, thereby permitting an exceedingly narrow catheter to be designed. In the case of a narrow submillimeter catheter, the linearly polarized light passes directly to the $O_2$-sensitive tip 68, whereas for larger diameter catheters the glass fiber 66 is mounted at the focal point of a collimating lens 70 which is used to provide uniform illumination of the catheter tip 68. The sealed $O_2$-sensitive tip 68 contains a quartz plate 72 which separates the optical components from the nonpolar viscous medium 74 in the tip 68. The catheter tip 68 contains a nonpolar viscous medium 74 such as paraffin or mineral oils in which pyrenebutyric acid or pyrene 76 is dissolved. Pyrene has a fluorescence lifetime approximately ten times that of pyrenebutyric acid or its salt form, thereby increasing the precision of the measurement, with an accuracy of $PO_2$ measurement of <1 mm Hg possible. The $O_2$-quenchable probe substance dissolved in a nonpolar viscous solvent is sealed within the catheter by an $O_2$ permeable membrane 78 such as polyethylene. A micro-thermistor 80 is also incorporated into the tip 68 of the catheter to allow simultaneous measurement of temperature, thus permitting temperature corrections to be performed according to the relation described in equation 4. Since optics are reversible, the linearly polarized fluorescence emission from the probe tip 68 returns along the single mode polarization-preserving glass fiber and is collected by the objective lens 64. Wavelengths >400 nm pass through the dichroic mirror 62 and wavelengths from 400–420 nm pass through an emission filter 82 to a Wollaston prism polarizer 84, which resolves the emitted fluorescence into its linearly polarized components parallel 86A and perpendicular 86B to the plane of excitation polarization. The vector components ($I_\parallel$ and $I_\perp$ are respectively and simultaneously detected by two optical detectors 88A and 88B, which can be photodiodes or photomultiplier tubes.

Figure 4:
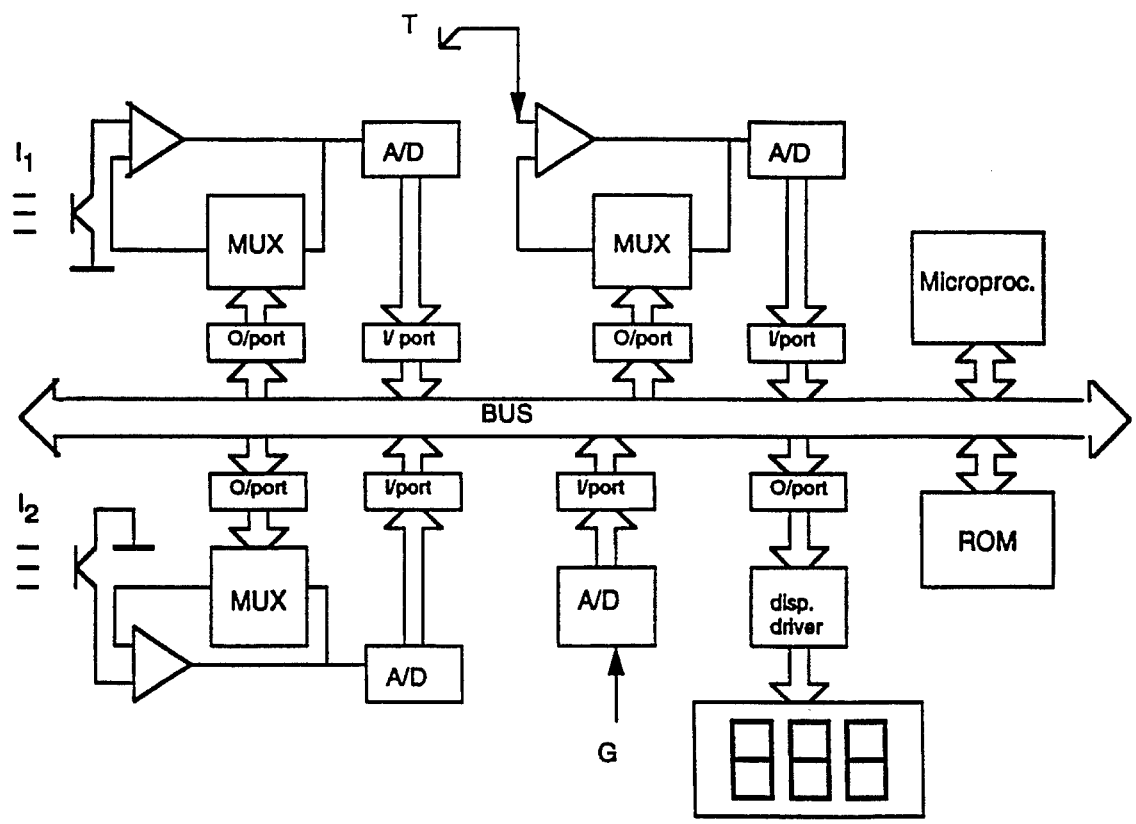
FIG. 4 is a schematic illustration of a data processor (of microprocessor design) which may be used to implement the calculations necessary to determine $PO_2$ at the catheter tip. MUX is a multiplexer; T is temperature, and G is an empirical constant used to correct for the dichroic mirror's transmission efficiency in the parallel and perpendicular planes for linearly polarized light. $I_1$ and $I_2$ are the resolved intensities of fluorescence emission respectively parallel and perpendicular to the plane of polarization of the excitation light.

Since the catheter design provides $PO_2$ measurement at a single locus, viz. at the catheter tip, anisotropy can be calculated from equation 7 and related to $PO_2$ according to equation 6, by means of a simple microprocessor design 90. Such a generic microprocessor design is illustrated in FIG. 4. Moreover, once the relations and constants employed in these equations are determined, they may be fixed and employed in every catheter manufactured, and each catheter need not be individually calibrated at the factory, or calibrated prior to its use in a clinical situation. This represents the considerable advantage of the present catheter design over previous designs which require constant recalibration in the factory as well as in the field.

EXAMPLE

To measure the topographic distribution of tissue $PO_2$ in retinal tissue, an imaging apparatus was set up as follows and as schematically illustrated in FIG. 2. A bovine eye was obtained from a local slaughterhouse and transported on ice to the laboratory. The isolated bovine eye was set up for normothermic arterial perfusion according to the procedures of de Coo, Zonnenberg and Trap (*Current Eye Research*, 12(4), 293–301, 1993), using oxygenated serum-free MEM (minimal essential medium) which was initially supplemented with 108 μM sodium pyrenebutyrate. After one hour of perfusion with MEM containing sodium pyrenebutyrate, the biocompatible, fluorescent probe substance reached equilibrium concentration in the retinal tissue, and the eye was subsequently perfused with oxygenated MEM alone during the period of time in which measurements of tissue $PO_2$ were performed. Corneal refraction was negated by a custom fundus lens made of UV transmitting glass (Optical Industries), and the retina was imaged first in visible light and a region of the retina selected which contained a retinal arteriole. Once proper orientation was established visible light was discontinued, and the retinal tissue was illuminated with linearly polarized ultraviolet light (UV). The radiant energy of a high pressure mercury bulb was gathered by a collector lens, was shuttered, and passed through a Clan-Thompson polarizer (Ealing, Inc.). The UV light was spectrally shaped by an excitation filter (340 nm peak, 25 nm half bandpass) and was then reflected by a dichroic mirror (Omega Optical) which reflects wavelengths <400 nm through an objective lens to the imaged retinal tissue. Emitted fluorescence (wavelengths >400 nm) from the excited tissue was gathered by the objective lens and passed through the dichroic mirror, and through an emission filter, which passed wavelengths from 400–420 nm to a Wollaston prism polarizer which resolved the emitted fluorescence into its linearly polarized components parallel and perpendicular to the plane of excitation polarization. The vector components ($I_\parallel$ and $I_\perp$ were respectively and simultaneously detected by the CCD (charge coupled devices) chips of two video cameras (Xybion model 250).

The vector components of fluorescence emission parallel and perpendicular to the plane of excitation polarization were digitized by the previously identified two digitizing boards within the previously identified computer operating at 66 MHz, and stored to hard disk (not shown). The computer software of Exhibit A was run on the computer to allow the variation of the slopes and offsets at each pixel location within the CCD arrays to be corrected by a correction file in the software, thereby ensuring uniform responsivity across the detector array. Similarly, the software allowed anisotropy to be calculated at a plurality of locations by means of equation 7 and converted to a two dimensional representation of tissue $PO_2$ by the application of equation 6 at each pixel locus. This procedure allowed the gathering of more than 300,000 values of retinal tissue $PO_2$ in space within approximately 33 milliseconds. The values for the constants used in equation 6 were previously determined during calibration experiments which involved the simultaneous measurement of tissue $PO_2$ by an oxygen microelectrode and by the indirect lifetime (anisotropy) system.

Figure 5A:
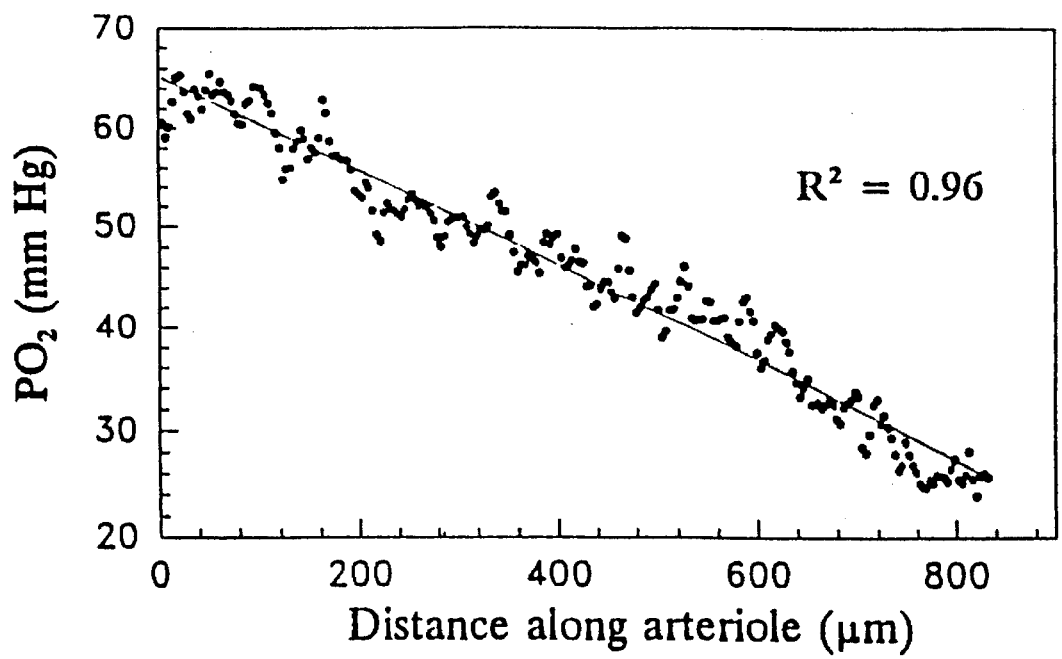
FIG. 5A is a graphical illustration of $PO_2$ levels measured parallel to a retinal arteriole within the retina of an isolated and perfused bovine eye, the longitudinal $PO_2$ drop parallel to the arteriole being fit to the function $\Delta PO_2 \propto M/(VD^2)$, the coefficient of determination being $R^2$.
Figure 5B:
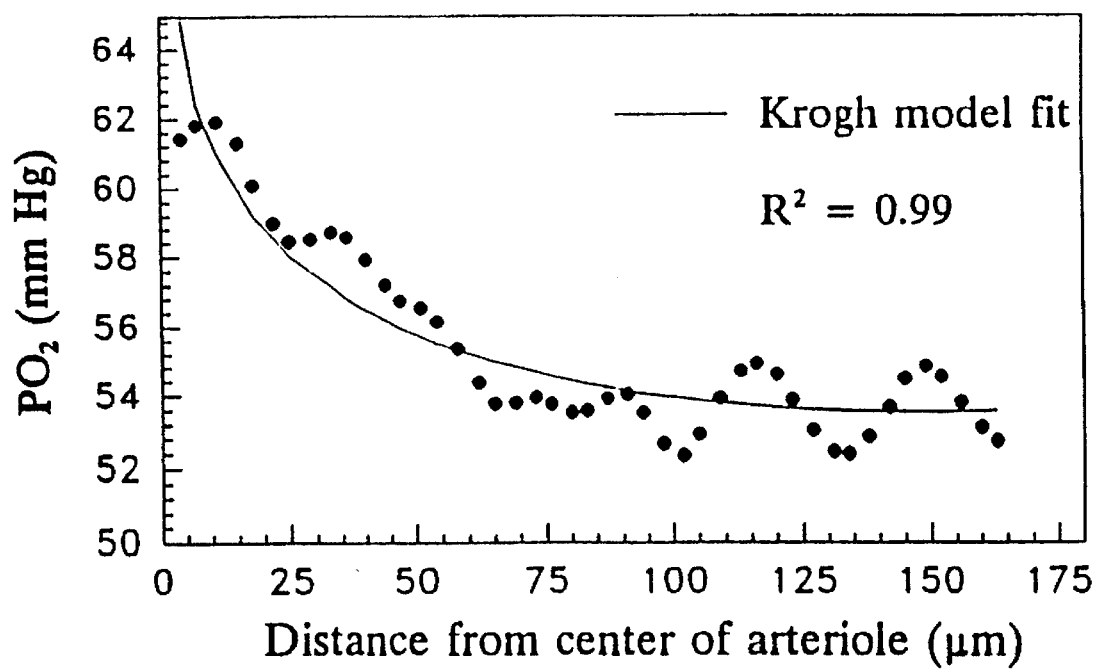
FIG. 5B is a graphical illustration of $PO_2$ levels measured perpendicular to a retinal arteriole within the retina of an isolated and perfused bovine eye, the $PO_2$ level perpendicular to the arteriole being fit to the Krogh mathematical model, the coefficient of determination being $R^2$.

To test the validity and precision of the system and the resultant optical map of retinal tissue $PO_2$, $PO_2$ gradients were measured both parallel and perpendicular to the retinal arteriole, as the mathematical functions describing these relationships can be predicted from oxygen diffusion mathematics, and are well established in the literature. The results of these measurements are shown in FIGS. 5A and 5B. Oxygen diffusion mathematics predicts that the longitudinal $PO_2$ drop in the tissue parallel to the arteriole should follow a linear relationship, whose slope is directly proportional to the oxygen consumption rate of the tissue (M) and inversely proportional to the velocity (V) of oxygen-containing solution within the arteriole times the square of the arteriolar diameter (D). As shown in FIG. 5A, the tissue $PO_2$ measurements along the length of the arteriole conform excellently to this well-established linear relationship, with a coefficient of determination ($R^2$) for a linear fit of 0.96 obtained; i.e., 96% of the variance in the data is accounted for by the expected linear fit. Similarly, the $PO_2$ gradient perpendicular to an arteriole should conform to a monotonically decreasing function which is described mathematically by the Krogh model. In FIG. 5A a Krogh model fit has been applied to the data with a goodness of fit ($R^2$) of 0.99; i.e., 99% of the variance in the data is accounted for by the expected mathematical relation. The data of FIGS. 5A and 5B, then, demonstrate that the indirect fluorescence lifetime system provides a noninvasive and valid method for evaluating tissue $PO_2$ in space and time.

While the present invention has been described in conjunction with preferred embodiments and illustrative examples, one skilled in the art after reading the foregoing specifications will be able to effect various changes, substitutions, and other alterations to the methods set forth herein. It is therefore intended that the protection granted by Letters Patent hereon be limited only by the definition contained in the appended claims and equivalents thereof.

Exhibit A

Source code excerpted from "Software for the Acquisition, Manipulation and Analysis of Video Images", © 1993, Biometric Imaging, Inc.

Please note that page numbers in this excerpt do not correspond to those in full document.

```c
/* initial grabber */ include <stdio.h>
include <dos.h> define BASEMEM 0xD000   /* memory base address */
define RB 0x300         /* pcplus register base address */ void ini_lut(void);
void ini_reg(void);

main()
{
int i;

ini_reg();
        ini_lut();

ini_reg();
        ini_lut();    /* why does it need twice ? */
} void ini_lut(void)
{
int j;
unsigned char i;

outp(RB+1,0x00);
for(j=0;j<=255;j++)
        {
                        i=j;
                        outp(RB+2,i);      outp(RB+3,i);       } outp(RB+1,0x01);
for(j=0;j<=255;j++)
        {
                        i=j;
                        outp(RB+2,i);      outp(RB+3,i);       } outp(RB+1,0x02);
for(j=0;j<=255;j++)
        {       i=j;
                        outp(RB+2,i);      outp(RB+3,i);       } outp(RB+1,0x03);
for(j=0;j<=255;j++)
        {       i=j;
                        outp(RB+2,i);      outp(RB+3,i);       }
} void ini_reg(void)
{ outp(RB,0x16);       outp(RB+1,3);              outp(RB+2,0);
outp(RB+3,0);        outp(RB+4,0x36);outp(RB+5,0x02);
outp(RB+6,0);        outp(RB+7,0);              outp(RB+8,0x40);
outp(RB+9,0);        outp(RB+10,0);             outp(RB+11,0);

}

/* clean the screen */
```

```
#include <stdio.h>
include <dos.h> define BP 0x3F8      /* for com1. baseport register address*/
define CONREG 0x300  /* pcplus regster base address */ main()
{
int i,j,k,line;
unsigned int stat,ini_stat;
unsigned char huge *mem;
unsigned char huge *mem_keep;

mem=mem_keep=(unsigned char huge *)MK_FP(0xD000,0);

ini_stat=0x16;

for(i=0;i<8;i++)
                {
                stat=(i<<5)&0xe0;
                stat |=ini_stat;
                outp(CONREG,stat);
                line=64;
                if(i==7) line=32;
                for(j=0;j<line;j++)
                        {
                        for(k=0;k<640;k++)
                                {
                                *mem=0;
                                mem++;
                                }
                        mem+=(1024-640);
                        }
                mem=mem_keep;
                }
}

/* This program is used to get integrating image from CCD camera.
   Integrate signal is a positive impulse sent from port 0x3FC (modem
   control register, DTR&RTS ON ),the snap signal from camera is sent
   to port 0x3FD (modem status register )              */ include <stdio.h>
include <dos.h>
#include <time.h>
#include <string.h>
#include <alloc.h>
include <dir.h> define BASEMEM 0xD000  /* memory base address */
define BP 0x3F8        /* for com1. baseport register address*/
define RB 0x300        /* pcplus regster base address */ main()
{
int m,j,test_times,x1,y1,x2,y2,th,tm,ts,av1,av2,img_num,re_openfile,time_delay;
float l,ii,sample_value,test_value,av,zeit_interval,zeit;
char imname[30],datname[30],s1[30],s2[30],s3[30],c,overwr;
FILE *fp,*datfile;
unsigned char *pixel,n,value;
unsigned char huge *mem;
long zz,zzz;
time_t anf_zeit,jetzt_zeit;
int odd,even,k;
struct ffblk ffblk;

printf("The datafile saves the information about your images,");
do{
```

```
        overwr='y';
        printf("\ninput the datafile name--> ");
        scanf("%s",datname);   printf("\n");
        if(findfirst(datname,&ffblk,0)==0)
                {
                printf("--- Warning: the file already exists, overwrite it?(y) ");
                overwr=getche();
                }
        }while(overwr!='y');

printf("\nThe name of your image has two attributes.\n");
        printf("the first is the NAME (e.g. 'myimage') given by user; \n");
        printf("the second is the IMAGE ORDER,(1,2,3,...) determined by the program.\n");
        printf("The image sequence will be myimage1,myimage2,......\n");
        printf("input image name--> ");
        scanf("%s",s1);          printf("\n");

datfile=fopen(datname,"wt");
                /* set output signal low */ mem=(unsigned char huge *)MK_FP(BASEMEM,0);

outp(BP+4,0);

/* initiate grabber's regsters */

/*              inigrab();
*/ c='';

*          do{
                if(c==3) exit();
                printf("\n-----------------------\n");

/* image grab */ value=inp(RB+5);
                outp(RB+5,value|0xc0);       /* for(j=0;j<10000;j++){}; */

/* get area of interested */ printf("if ready, type 'f' to freeze image and get AOI:");
                while((c=getche())!='f')      {         if(c==3) exit();         };
                printf("\n");
                outp(RB+5,0x82);     /* do snap */ getaoi(&x1,&y1,&x2,&y2);
                x1++;     y1++;     x2--;      y2--;
                area_ave(x1,y1,x2,y2,&av);
                printf("the area size is %d X %d. average value is %f.\n",
                        x2-x1+1,y2-y1+1,av);
                printf("AIO is OK?(y)");

}while((c=getche())!='y');

fprintf(datfile,"AOI size:(%d x %d); rectangular position: [(%d,%d),(%d,%d)].\n",
                x2-x1+1,y2-y1+1,x1-1,y1-1,x2+1,y2+1);
                printf("\n");

img_num=0;
                time_delay=0;
        do{

/*              inigrab();
*/              outp(BP+4,0);
                value=inp(RB+5);
                outp(RB+5,value|0xc0);        /* do grab again */
```

```c
/* input integrateduration */ printf("--------------------------------------------------------\n");
if(time_delay==0)
        {
        printf("Delay time(sec.): ");
        scanf("%f",&zeit);      printf("\n");
        time_delay=1;
        }
else
        {
        printf("delay time: %f sec., change it?(y): ",zeit);
        if(getche()=='y')
                {
                printf("\ndelay time(sec.): ");
                scanf("%f",&zeit);
                }
        printf("\n");
        }
i=zeit;
ii=i;
test_times=0;
do{ i=ii;
outp(RB,0x16); value=inp(RB+5); outp(RB+5,value|0xc0);

/* output integrating impulse */

/*      printf("integrating......");
        i*=25000;
*/ i*=100000;
while(i>0)
        {
        outp(BP+4,3);                   /* set output signal high */
        i--;
        }
outp(RB+5,0x82);
for(i=0;i<10000;i++){}                  /* for 386 i<1000 */ outp(BP+4,0);           /* set output signal low */

/* wait for grab signal */ while(inp(BP+6)==1)             {       };

/* get test value, if integrate not successful, do again */ outp(RB,((5<<5)&0xe0) | 0x16);
test_value=100;
test_times++;
}while(test_value<10 && test_times<=2.);

/* store image into disk*/
show_time(&th,&tm,&ts,&jetzt_zeit);
area_ave(x1,y1,x2,y2,&av);
rectangular_show(x1-1,y1-1,x2+1,y2+1,255);
av=(2*av<255)? 2*av:255;
av1=av;             av*=100;   av2=av;                  av1*=100;
av1=av2-av1;        av2/=100;  av/=100;
outp(RB,(((1<<5)&0xe0)|0x16));

/*      for(k=0;k<40;k++)
        {
        zz=1024;  zz*=k;        zz+=10;
        printf("%d ",*(mem+zz+10));
        }
printf("\n");
```

```
*/
odd=even=0;
for(k=0;k<50;k++)
        {
        odd+=*(mem+k);    even+=*(mem+k+1024);
        }
if(odd>even)      printf("------this is the ODD field image.\n",odd,even);
else      printf("------this is the EVEN field image.\n",odd,even);
printf("------average value is %d.%d, store image?(y) ",av2,av1);
if(getche()=='y')
        {
        img_num++;
        printf("\n");
        if(img_num==1)      anf_zeit=jetzt_zeit;
        zeit_interval=jetzt_zeit-anf_zeit;
        zeit_interval/=60;
        do{
                    overwr='y';
                    itoa(img_num,s2,10);
                    strcpy(imname,s1);
                    strcat(imname,s2);
                    re_openfile=0;
                    printf("the name of image %d is < %s >, change it(y): ",
                                    img_num,imname);
                    if(getche()=='y')
                            {
                            printf("\nnew name: ");
                            scanf("%s",imname);
                            }
                    printf("\n");
                    if(findfirst(imname,&ffblk,0)==0)
                            {
                            printf("--- Warning: the file already exists, overwrite it?(y) ");
                            overwr=getche();
                            }
        }while(overwr!='y');

fp=fopen(imname,"wb");
        im_store(fp,x1,y1,x2,y2);
        fclose(fp);
        if(odd>even)
        fprintf(datfile,"-- %s: mean_value(%f), time(%f min.), odd field.\n",
                    imname,av,zeit_interval);
        else
        fprintf(datfile,"-- %s: mean_value(%f), time(%f min.), even field.\n",
                    imname,av,zeit_interval);
        } printf("\n");
        printf("Press q to quit, any other key to continue.\n");

}while(getche()!='q');

fclose(datfile);
printf("\n");

} inigrab()
{
outp(RB,0x16);      outp(RB+1,3);      outp(RB+2,0);
outp(RB+3,0);       outp(RB+4,36);     outp(RB+5,0x02);
outp(RB+6,0);       outp(RB+7,0);      outp(RB+8,0x40);
outp(RB+9,0);       outp(RB+10,0);     outp(RB+11,0);
} define CONREG 0x300 getaoi(x1,y1,x2,y2)
```

```
int *x1,*y1,*x2,*y2;
{
float xx1,yy1,xx2,yy2;

start_end_point(&xx1,&yy1,&xx2,&yy2);

*x1=xx1;  *y1=yy1;  *x2=xx2;  *y2=yy2;
rectangular_show(*x1,*y1,*x2,*y2,255);

} rectangular_show(x1,y1,x2,y2,br)
int x1,y1,x2,y2,br;
{
line_show(x1,y1,x2,y1,br);
line_show(x2,y1,x2,y2,br);
line_show(x2,y2,x1,y2,br);
line_show(x1,y1,x1,y2,br);
} area_ave(x1,y1,x2,y2,av)
int x1,y1,x2,y2;
float *av;
{
int i,j,x,y,k,start_line,end_line,start_blc,end_blc,
        start_y_offset,end_y_offset,line_offset;
unsigned char huge *mem;
unsigned char huge *mem_keep;
unsigned char ini_stat,stat;
unsigned char p;
long zz,zzz,testv1,testv2;

mem=(unsigned char huge *)MK_FP(BASEMEM,0);
            x=x2-x1+1;
            start_blc=y1/64;            end_blc=(y2+1)/64;
            start_y_offset=y1%64;       end_y_offset=(y2+1)%64;
            mem_keep=mem+x1;
            zz=start_y_offset;    zz*=1024;  zz+=x1;
            mem +=zz;

/* fine the data line */
            testv1=testv2=0;
            for(i=0;i<x;i++)
                    {
                    testv1+=*(mem+i);   testv2+=*(mem+1024+i);
                    }
            line_offset=(testv1>testv2)? 0:1;

ini_stat=0x16;              zzz=zz=0;
            for(i=start_blc;i<=end_blc;i++)
                    {
                    stat=(i<<5)&0xe0;
                    stat |=ini_stat;
                    outp(CONREG,stat);

if(i==start_blc)
                            start_line=start_y_offset+line_offset;
                    else    start_line=0+line_offset;
                    if(i==end_blc) end_line=end_y_offset;
                    else       end_line=64;

for(j=start_line;j<end_line;j+=2)
                            {
                            for(k=0;k<x;k++)
                                    {
                                    zzz+=*mem;        zz++;
                                    mem++;
                                    }
                            mem+=(1024-x);
```

```
                                    }
                        mem=mem_keep;
                }

*av=zzz;      *av/=zz;

} point_show(xp,yp,br)
int xp,yp,br;
{
unsigned char huge *mem;
int block,y_offset;
unsigned char status;
long zz;

mem=(unsigned char huge *)MK_FP(BASEMEM,0);
block=yp/64;         y_offset=yp%64;
zz=1024;   zz*=y_offset;         zz+=xp;           mem+=zz;
status=((block<<5)&0xe0)|0x16;
outp(CONREG,status);   *mem=br;
} line_show(x1,y1,x2,y2,br)
int x1,y1,x2,y2,br;
{
/*      start(small address)------------>end(big address)      */
int p,xx,yy,q,aa,delta_x,delta_y;
float qq,dx,dy;
long zzz,zz;

zz=y1;        zz*=1024;  zz+=x1;
zzz=y2;       zzz*=1024;           zzz+=x2;
if(zz>zzz)
        {
        xx=x1;       x1=x2;      x2=xx;
        yy=y1;       y1=y2;      y2=yy;
        }
delta_x=x2-x1;                    delta_y=y2-y1;

/*printf("delta_x: %f %d %d ,delta_y: %f %d %d.\n",delta_x,x2,x1,delta_y,y2,y1);
*/ if(delta_x==0)
        for(p=0;p<=delta_y;p++)             point_show(x1,y1+p,br);
if(delta_y==0)
        for(p=0;p<=delta_x;p++)             point_show(x1+p,y1,br);
if(delta_x!=0 && delta_y!=0)
        {
        aa=(delta_x>0)?1:-1; dx=delta_x;         dy=delta_y;
        if(aa*delta_x >= delta_y)
                for(p=0;p<=aa*delta_x;p++)
                        {
                        qq=(dy*p)/(dx*aa)+0.5;           q=qq;
                        point_show(x1+aa*p,y1+q,br);
                        }
        else
                for(p=0;p<delta_y;p++)
                        {
                        qq=(dx*p)/(aa*dy)+aa*0.5;         q=qq;
                        point_show(x1+q,y1+p,br);
                        }
/*      printf("--draw show ok.\n");
        */
        }
}
```

```
define CONREG 0x300 start_end_point(x1,y1,x2,y2)
float *x1,*y1,*x2,*y2;
{
unsigned char huge *cross_buf;
char b[4];
int a,i,j,x,y,xx,yy,kx,ky,sx,sy,ex,ey;

x=320;    y=240;

cross_buf=(unsigned char huge *)calloc(41,1);

for(i=0;i<2;i++)
        {
        xx=x;     yy=y;
        do{
        if(i==0)  printf("current position---(%1d,%1d).\r",xx,yy);
        if(i==1)
                {
                printf("current position---(%1d,%1d), AOI size (%1d,%1d).\r",
                        xx,yy,xx-sx-1,yy-sy-1);
                if(xx-sx-1<0 || yy-sy-1<0)
                        {
                        sound(600);         delay(100); nosound();
                        }
                }
        kx=xx;    ky=yy;
        move_cross(kx,ky,cross_buf);
        a=getch();
        if(a==56) yy--;
        if(a==57) yy-=10;

if(a==50) yy++;
        if(a==49) yy+=10;

if(a==52) xx--;
        if(a==55) xx-=10;

if(a==54) xx++;
        if(a==51) xx+=10;

if(a==48) {         xx=320;    yy=240;   } if(a>=48 && a<=57)          recover_cross(kx,ky,cross_buf);
        }while(a!=43);
        if(i==0)
                {
                sx=xx;    sy=yy;    point_show(sx,sy,255);
                *x1=xx;             *y1=yy;
                printf("\nup-left point(%d,%d).\n",sx,sy);
                }
        if(i==1)
                {
                ex=xx;    ey=yy;    point_show(ex,ey,255);
                *x2=xx;             *y2=yy;
                printf("\nlow-right point(%d,%d).\n",ex,ey);
                }
        }
} move_cross(xp,yp,cross_buf)
int xp,yp;
unsigned char huge *cross_buf;
{
int i,xx,yy;
unsigned char huge *mem;
unsigned char huge *mem_keep;
int block,y_offset;
```

```
unsigned char status;
long zz;

mem=mem_keep=(unsigned char huge *)MK_FP(BASEMEM,0);
for(i=-10;i<=10;i++)
        {
        yy=yp+i;    xx=xp;
        block=yy/64;           y_offset=yy%64;
        zz=1024;   zz*=y_offset;        zz+=xx;         mem+=zz;
        status=((block<<5)&0xe0)|0x16;
        outp(CONREG,status);
        *cross_buf=*mem;    *mem=255;       cross_buf++;
        mem=mem_keep;
        } mem=mem_keep;
block=yp/64;           y_offset=yp%64;
status=((block<<5)&0xe0)|0x16;
outp(CONREG,status);
for(i=-10;i<=10;i++)
        {
        mem=mem_keep;    xx=xp+i;
        zz=1024;   zz*=y_offset;        zz+=xx;         mem+=zz;
        if(i!=0)
                {
                *cross_buf=*mem;    *mem=255;       cross_buf++;
                }
        }
} recover_cross(xp,yp,cross_buf)
int xp,yp;
unsigned char huge *cross_buf;
{
int i,xx,yy;
unsigned char huge *mem;
unsigned char huge *mem_keep;
int block,y_offset;
unsigned char status;
long zz;

mem=mem_keep=(unsigned char huge *)MK_FP(BASEMEM,0);
for(i=-10;i<=10;i++)
        {
        mem=mem_keep;
        yy=yp+i;    xx=xp;
        block=yy/64;           y_offset=yy%64;
        zz=1024;   zz*=y_offset;        zz+=xx          mem+=zz;
        status=((block<<5)&0xe0)|0x16;
        outp(CONREG,status);
        *mem=*cross_buf;    cross_buf++;
        }
mem=mem_keep;
block=yp/64;           y_offset=yp%64;
status=((block<<5)&0xe0)|0x16;
outp(CONREG,status);
for(i=-10;i<=10;i++)
        {
        mem=mem_keep;
        xx=xp+i;
        zz=1024;   zz*=y_offset;        zz+=xx;         mem+=zz;
        if(i!=0)
                {
                *mem=*cross_buf;    cross_buf++;
                }
        }
} im_store(fp,x1,y1,x2,y2)
```

```
FILE *fp;
int x1,y1,x2,y2;
{
int i,j,x,y,k,start_line,end_line,start_blc,end_blc,
        start_y_offset,end_y_offset;
unsigned char huge *mem;
unsigned char huge *mem_keep;
unsigned char ini_stat,stat;
unsigned char p;
long zz;
char ix[8],iy[8];

mem=(unsigned char huge *)MK_FP(BASEMEM,0);
        x=x2-x1+1;              y=y2-y1+1;
        itoa(x,ix,10);          itoa(y,iy,10);
        for(i=0;i<8;i++)        fputc(ix[i],fp);
        for(i=0;i<8;i++)        fputc(iy[i],fp);
        start_blc=y1/64;                end_blc=(y2+1)/64;
        start_y_offset=y1%64;           end_y_offset=(y2+1)%64;
        mem_keep=mem+x1;
        zz=start_y_offset;      zz*=1024;       zz+=x1;
        mem+=zz;
        ini_stat=0x16;
        for(i=start_blc;i<=end_blc;i++)
                {
                stat=(i<<5)&0xe0;
                stat |=ini_stat;
                outp(CONREG,stat);

if(i==start_blc)        start_line=start_y_offset;
                        else            start_line=0;
                if(i==end_blc) end_line=end_y_offset;
                        else            end_line=64;
                for(j=start_line;j<end_line;j++)
                        {
                        for(k=0;k<x;k++)
                                {
                                p=*mem;         fputc(p,fp);
                                mem++;
                                }
                        mem+=(1024-x);
                        }
                mem=mem_keep;

}
printf("------ a %d X %d image is saved.\n",x,y);
} include <time.h> show_time(th,tm,ts,jetzt_zeit)
int *th,*tm,*ts;
time_t *jetzt_zeit;
{
struct tm *timeptr;
time_t    secsnow;

time(&secsnow);         *jetzt_zeit=secsnow;
timeptr=localtime(&secsnow);
printf("------current time is %02d:%02d:%02d\n",
        timeptr->tm_hour,timeptr->tm_min,timeptr->tm_sec);
*th=timeptr->tm_hour;
*tm=timeptr->tm_min;
*ts=timeptr->tm_sec;
} include "ypdef.h"
include <stdio.h>
#include <string.h>
```

```c
#include <dos.h>
include <alloc.h> define BASEMEM 0xD000
define CONREG 0x300 main()
{
char imname[30],outname[30],calname1[30],calname2[30];
unsigned char huge *image;
unsigned char huge *stdimage1;
unsigned char huge *stdimage2;
long zz;
int x,y,i,j,pp,field;
float ave0,ave1,ave2,ave3,p0,p1,p2,k,b;

do{
printf("1. image with one field.\n");
printf("2. image with both fields.\n");
scanf("%d",&field);    printf("\n");
}while(field!=1 && field!=2);
printf("image name: ");
scanf("%s",imname);   printf("\n");
printf("calibration image 1: ");
scanf("%s",calname1);  printf("\n");
printf("calibration image 2: ");
scanf("%s",calname2);  printf("\n");

/*
zz=y;     zz*=x;
image=(unsigned char huge *)farcalloc(zz,1);
stdimage1=(unsigned char huge *)farcalloc(zz,1);
stdimage2=(unsigned char huge *)farcalloc(zz,1);
if(image==NULL || stdimage1==NULL || stdimage2==NULL )
        {       printf("fail to allocate.\n");    exit(1);   }

*/
stdimage1=(unsigned char huge *)read_image(calname1,&x,&y);
image_show(stdimage1,0,0,x,y);
stdimage2=(unsigned char huge *)read_image(calname2,&x,&y);
image_show(stdimage2,50,50,x,y);
image=(unsigned char huge *)read_image(imname,&x,&y);
image_show(image,100,100,x,y);

ave1=ave2=0;
for(j=0;j<y;j++)
         for(i=0;i<x;i++)
                {
                zz=j;      zz*=x;    zz+=i;
                ave1+=*(stdimage1+zz);
                ave2+=*(stdimage2+zz);
                }
ave1/=x;   ave1/=y;
ave2/=x;   ave2/=y;
if(field==1)
         {      ave1*=2;  ave2*=2;  }
printf("the average value of cal-image 1: %f.\n",ave1);
printf("the average value of cal-image 2: %f.\n",ave2);
if(ave1==ave2)
         {
         printf("same average value.\n");
         exit();
         }
ave0=ave3=0;
for(j=0;j<y;j++)
         for(i=0;i<x;i++)
                {
                zz=j;      zz*=x;    zz+=i;
                p0=*(image+zz);              ave3+=p0;
```

```
                    p1=*(stdimage1+zz);
                    p2=*(stdimage2+zz);
                    k=(p1-p2)/(ave1-ave2);           b=p2-k*ave2;
                    if(k!=0)   p0=(p0-b)/k+0.5;
                    ave0+=p0;
                    pp=p0;
                    if(pp>=255)        pp=255;
                    if(pp<=0)  pp=0;
                    point_show(i+150,j+150,pp);
                    }
ave0/=x;   ave0/=y;
ave3/=x;   ave3/=y;
printf("the average value of the image to be calibrated: %f.\n",ave3);
printf("the average value of the calibrated image: %f.\n",ave0);
printf("\n");

printf("save image?(y): ");
if(getche()=='y')
          {
          printf("\noutput image name: ");
          scanf("%s",outname);  printf("\n");
          save_image(outname,150,150,150+x-1,150+y-1);
          }
printf("\n===================== END =============================\n");

}

/*............. substract image2 from image1 ............*/ include "ypdef.h"
include <stdio.h>
include <dos.h>
include <alloc.h>
include <dir.h> define BASEMEM 0xD000
define CONREG  0x300 main ()
{
char imgname1[50],imgname2[50],outname[50],overwr;
unsigned char huge *image;
unsigned char huge *board;
unsigned char huge *p;
int choice,c,i,j,x,y,ws,wrongname,pp,ppp;
long size,zz;
int n;
float s,s1,s2,s3;
struct ffblk ffblk;

/* read an image from disk into memory */ printf("%lu bytes free in ram.\n",farcoreleft());
printf("           Image1 - Image2                  \n");
printf(" Polarization= ---------------- X Scale_factor   \n");
printf("           Image1 + Image2                  \n");
printf("\n");
printf("the names of image1, image2, and scale_factor: ");
scanf("%s %s %f",imgname1,imgname2,&s);
printf("\n");

image=(unsigned char huge *)read_image(imgname1,&x,&y);
image_show(image,0,0,x,y);
farfree((unsigned char far *)image);

p=(unsigned char huge *)farcalloc(1,1);
image=(unsigned char huge *)read_image(imgname2,&x,&y);
for(j=0;j<y;j++)
          for(i=0;i<x;i++)
```

```c
                {
                zz=j;       zz*=x;      zz+=i;
                get_point_value(i,j,p);  pp=*p;
                ppp=*(image+zz);
                s1=pp;      s2=ppp;             s3=s*(s1-s2)/(s1+s2)+0.5;
                pp=s3;
                if(pp>255) pp=255;              if(pp<0)    pp=0;
                point_show(i,j,pp);
                }
printf("save image?(y): ");
if(getche()=='y')
        {
        do{
        overwr='y';
        printf("\noutput image name: ");
        scanf("%s",outname);  printf("\n");
        if(findfirst(outname,&ffblk,0)==0)
                {
                printf("--- Warning: the file already exists, overwrite it?(y) ");
                overwr=getche();
                }
        }while(overwr!='y');
        printf("\n");
        save_image_screen(outname,0,0,x-1,y-1);
        }
} save_image_screen(imname,x1,y1,x2,y2)
char imname[50];
int x1,y1,x2,y2;
{
int wrongname,i,j,x,y,k,start_line,end_line,start_blc,end_blc,
        start_y_offset,end_y_offset;
unsigned char huge *mem;
unsigned char huge *mem_keep;
unsigned char ini_stat,stat;
unsigned char p;
long zz;
FILE *fp;
char ix[8],iy[8];

do{
wrongname=0;
if((fp=fopen(imname,"wb"))==NULL)
        {
        wrongname=1;
        printf("wrong name! try again: ");
        scanf("%s",imname);    printf("\n");
        }
}while(wrongname==1);
mem=(unsigned char huge *)MK_FP(BASEMEM,0);
x=x2-x1+1;       y=y2-y1+1;
itoa(x,ix,10);       itoa(y,iy,10);
for(i=0;i<8;i++)       fputc(ix[i],fp);
for(i=0;i<8;i++)       fputc(iy[i],fp);

start_blc=y1/64;           end_blc=(y2+1)/64;
start_y_offset=y1%64;      end_y_offset=(y2+1)%64;
mem_keep=mem+x1;
zz=start_y_offset;    zz*=1024;     zz+=x1;
mem +=zz;
        ini_stat=0x16;
        for(i=start_blc;i<=end_blc;i++)
                {
                stat=(i<<5)&0xe0;
                stat |=ini_stat;
                outp(CONREG,stat);

if(i==start_blc)     start_line=start_y_offset;
```

```
                    else    start_line=0;
        if(i==end_blc) end_line=end_y_offset;
                    else    end_line=64;
        for(j=start_line;j<end_line;j++)
            {
            for(k=0;k<x;k++)
                {
                p=*mem;     fputc(p,fp);
                mem++;
                }
            mem+=(1024-x);
            }
        mem=mem_keep;

}
printf("----- a %d X %d image %s is saved.\n",x,y,imname);
} include "ypdef.h"
include <stdio.h>
include <alloc.h>
include <dos.h>
include <math.h> define BASEMEM 0xD000
define CONREG 0x300 define XO 320
define YO 240 main()
{
char imname[30],outname[30];
unsigned char huge *image;
int i,j,x,y,t1,t2;
long size,*hist;

hist=(long *)calloc(256,sizeof(long));
        printf("%lu bytes free.\n",farcoreleft());
        printf("image name: ");
        scanf("%s",imname);     printf("\n");
        ini_reg();
        ini_lut();
        image=(unsigned char huge *)read_image(imname,&x,&y);
        image_show(image,XO-x/2,YO-y/2,x,y);
        histogram_image(image,x,y,hist);
        /*
        for(j=0;j<480;j++)
                for(i=533;i<567;i++) point_show(i,j,0);
        grey_level_show();
        show_hist_vertical(hist);           */
        move_cursor_equalize(image,x,y,&t1,&t2,hist);
        equalize_mem(image,x,y,t1,t2);
        printf("\nsave image?(y): ");
        if(getche()=='y')
                {
                printf("\noutput equalized image name: ");
                scanf("%s",outname);    printf("\n");
                save_image(outname,XO-x/2,YO-y/2,XO-x/2+x-1,YO-y/2+y-1);
                } printf("\n");

} define CONREG 0x300 move_cursor_equalize(image,x,y,t1,t2,hist)
unsigned char huge *image;
```

```
int x,y,*t1,*t2;
long *hist;
{
unsigned char huge *cross_buf;
char b[4];
int a,i,j,t,xx,yy,kx,ky,sx,sy,ex,ey,k1,k2;
float tt;

cross_buf=(unsigned char huge *)calloc(41,1);
xx=610;    yy=240;
printf("move cursor to get threshold.");

do{
          for(k2=0;k2<480;k2++)
                    for(k1=533;k1<639;k1++)   point_show(k1,k2,0);
          grey_level_show();
          show_hist_vertical(hist);

printf("\n");
          for(i=0;i<2;i++)
          {
                    if(i==0)    printf("move cursor to LOW cut-off grey level.\n");
                    else                printf("move cursor to HIGH cut-off grey level.\n");
                    do{
                    tt=255;    tt*=yy;   tt/=480;   t=tt;
                    printf("current threshold--- %d .\r",t);
                    kx=xx;      ky=yy;
                    save_move_cross(kx,ky,cross_buf);
                    a=getch();
                    if(a==56)  yy--;
                    if(a==57)  yy-=10;

if(a==50)  yy++;
                    if(a==49)  yy+=10;

if(a==48)  yy=240;

recover_cross(kx,ky,cross_buf);
                    }while(a!=43);
                    if(i==0)    *t1=yy;
                    else        *t2=yy;
                    printf("\n");
          }
          tt=255;    tt*=*t1;  tt/=480;   *t1=tt;
          tt=255;    tt*=*t2; tt/=480;   *t2=tt;
          equalize_screen(image,x,y,*t1,*t2);
          printf("\nOK?(y): ");
}while(getche()!='y');

} save_move_cross(xp,yp,cross_buf)
int xp,yp;
unsigned char huge *cross_buf;
{
int i,xx,yy;
unsigned char huge *mem;
unsigned char huge *mem_keep;
int block,y_offset;
unsigned char status;
long zz;

mem=mem_keep=(unsigned char huge *)MK_FP(BASEMEM,0);
for(i=-10;i<=10;i++)
          {
          yy=yp+i;   xx=xp;
          block=yy/64;         y_offset=yy%64;
          zz=1024;   zz*=y_offset;        zz+=xx;              mem+=zz;
          status=((block<<5)&0xe0)|0x16;
```

```
                outp(CONREG,status);
                *cross_buf=*mem;    *mem=255;       cross_buf++;
                mem=mem_keep;
                } mem=mem_keep;
block=yp/64;            y_offset=yp%64;
status=((block<<5)&0xe0)|0x16;
outp(CONREG,status);
for(i=-10;i<=10;i++)
        {
        mem=mem_keep;   xx=xp+i;
        zz=1024;   zz*=y_offset;        zz+=xx;         mem+=zz;
        if(i!=0)
                {
                *cross_buf=*mem;    *mem=255;       cross_buf++;
                }
        }
} recover_cross(xp,yp,cross_buf)
int xp,yp;
unsigned char huge *cross_buf;
{
int i,xx,yy;
unsigned char huge *mem;
unsigned char huge *mem_keep;
int block,y_offset;
unsigned char status;
long zz;

mem=mem_keep=(unsigned char huge *)MK_FP(BASEMEM,0);
for(i=-10;i<=10;i++)
        {
        mem=mem_keep;
        yy=yp+i;   xx=xp;
        block=yy/64;            y_offset=yy%64;
        zz=1024;   zz*=y_offset;        zz+=xx;         mem+=zz;
        status=((block<<5)&0xe0)|0x16;
        outp(CONREG,status);
        *mem=*cross_buf;    cross_buf++;
        }
mem=mem_keep;
block=yp/64;            y_offset=yp%64;
status=((block<<5)&0xe0)|0x16;
outp(CONREG,status);
for(i=-10;i<=10;i++)
        {
        mem=mem_keep;
        xx=xp+i;
        zz=1024;   zz*=y_offset;        zz+=xx;         mem+=zz;
        if(i!=0)
                {
                *mem=*cross_buf;    cross_buf++;
                }
        }
} grey_level_show()
{
int i,j,grey;
float g;

for(j=0;j<480;j++)
        {
        g=j;    g*=255;         g/=480;         grey=g;
        for(i=610;i<640;i++)
                {
                point_show(i,j,grey);
```

```
        }
    }
number_display(0,578,6,7,9,255);        line_show(567,0,571,0,255);
                                        line_show(606,0,609,0,255);
number_display(3,578,60,7,9,255);
number_display(1,587,60,7,9,255);
                                        line_show(567,60,571,60,255);
                                        line_show(606,60,609,60,255);
number_display(6,578,120,7,9,255);
number_display(3,587,120,7,9,255);
                                        line_show(567,120,571,120,255);
                                        line_show(606,120,609,120,255);
number_display(9,578,180,7,9,255);
number_display(5,587,180,7,9,255);
                                        line_show(567,180,571,180,255);
                                        line_show(606,180,609,180,255);
number_display(1,578,240,7,9,255);
number_display(2,587,240,7,9,255);
number_display(7,596,240,7,9,255);
                                        line_show(567,240,571,240,255);
                                        line_show(606,240,609,240,255);
number_display(1,578,300,7,9,255);
number_display(5,587,300,7,9,255);
number_display(9,596,300,7,9,255);
                                        line_show(567,300,571,300,255);
                                        line_show(606,300,609,300,255);
number_display(1,578,360,7,9,255);
number_display(9,587,360,7,9,255);
number_display(1,596,360,7,9,255);
                                        line_show(567,360,571,360,255);
                                        line_show(606,360,609,360,255);
number_display(2,578,420,7,9,255);
number_display(2,587,420,7,9,255);
number_display(3,596,420,7,9,255);
                                        line_show(567,420,571,420,255);
                                        line_show(606,420,609,420,255);
number_display(2,578,474,7,9,255);
number_display(5,587,474,7,9,255);
number_display(5,596,474,7,9,255);
                                        line_show(567,479,571,479,255);
                                        line_show(606,479,609,479,255);
} equalize_screen(image,x,y,t1,t2)
unsigned char huge *image;
int x,y,t1,t2;
{
int i,j,p,t;
long zz;
float k,b,w;

/*              function w=[255/(t2-t1)] *(b-t1)              */ if(t1>t2) {     t=t1;   t1=t2;  t2=t;   }
k=255;          k/=(t2-t1);

for(j=YO-y/2;j<YO-y/2+y;j++)
    {
        for(i=XO-x/2;i<XO-x/2+x;i++)
        {
            zz=j-(YO-y/2);  zz*=x;  zz+=(i-(XO-x/2));
            p=*(image+zz);
            if(p<=t1) point_show(i,j,0);
            if(p>=t2) point_show(i,j,254);
            if(p>t1 && p<t2)
            {
                b=p-t1;  b*=k;   p=b;
                point_show(i,j,p);
            }
```

```
                    }
            }
printf("\npress any key to display new color scale.\n");
getch();
equalized_grey_level_show(t1,t2);

} equalize_mem(image,x,y,t1,t2)
unsigned char huge *image;
int x,y,t1,t2;
{
int i,j,t,p;
long zz;
float k,w,b;

if(t1>t2)   {       t=t1;       t1=t2;      t2=t;       }
k=255;              k/=(t2-t1);

for(j=0;j<y;j++)
        {
            for(i=0;i<x;i++)
                {
                    zz=j;       zz*=x;      zz+=i;
                    p=*(image+zz);
                    if(p<=t1)  *(image+zz)=0;
                    if(p>=t2)  *(image+zz)=254;
                    if(p>t1 && p<t2)
                        {
                            w=p-t1;             w*=k;       p=w;
                            *(image+zz)=p;
                        }
                }
        }
} define BASEMEM 0xD000  /* memory base address */
define RB 0x300         /* pcplus regster base address */ ini_lut(void)
{
int j;
unsigned char i,ii;

/* initialize bank 0 to linear */ outp(RB+1,0x00);
for(j=0;j<=255;j++)
        {           i=j;
                    outp(RB+2,i);       outp(RB+3,i);       } outp(RB+1,0x01);
for(j=0;j<=255;j++)
        {
                    i=j;
                    outp(RB+2,i);       outp(RB+3,i);       } outp(RB+1,0x02);
for(j=0;j<=255;j++)
        {       i=j;
                    outp(RB+2,i);       outp(RB+3,i);       } outp(RB+1,0x03);
for(j=0;j<=255;j++)
        {           i=j;
                    outp(RB+2,i);       outp(RB+3,i);       }

/* initialize bank 4 to bit-plane-oriented        */
```

```
outp(RB+1,0x82);
for(j=0;j<=255;j++)
        {       i=j;        outp(RB+2,i);
                ii=0;
                if(i<64 && i>0)                    ii=128;
                if(i>=64 && i<=128)    ii=128-2*(i-64);
                if(i==255)         ii=128;
                /*
                if( (i & 0x01)==1)    ii=36;
                if( (i & 0x02)==2)    ii=72;
                if( (i & 0x03)==3)    ii=108;
                if( (i & 0x04)==4)    ii=144;
                if( (i & 0x05)==5)    ii=180;
                if( (i & 0x06)==6)    ii=216;
                if( (i & 0x07)==7)    ii=252;
                */ outp(RB+3,ii);
        } printf("\n");

outp(RB+1,0x81);
for(j=0;j<=255;j++)
        {       i=j;        outp(RB+2,i);
                ii=0;
                if(i<64 && i>0)                    ii=i*2;
                if(i>=64 && i<192)    ii=128;
                if(i>=192)         ii=128-2*(i-192);
                if(i==254)         ii=0;
                if(i==255)         ii=128;
                /*
                if( (i & 0x08)==0x08) ii=36;
                if( (i & 0x10)==0x10) ii=72;
                if( (i & 0x18)==0x18) ii=108;
                if( (i & 0x20)==0x20) ii=144;
                if( (i & 0x28)==0x28) ii=180;
                if( (i & 0x30)==0x30) ii=216;
                if( (i & 0x38)==0x38) ii=252;
                */
                outp(RB+3,ii);
        }
printf("\n");

outp(RB+1,0x80);
for(j=0;j<=255;j++)
        {       i=j;        outp(RB+2,i);
                ii=0;
                if(i>128 && i<192)    ii=2*(i-128);
                if(i>=192)         ii=128;
                if(i==254)         ii=220;
                /*
                if( (i & 0x40)==0x40) ii=85;
                if( (i & 0x80)==0x80) ii=170;
                if( (i & 0xc0)==0xc0) ii=255;
                */
                outp(RB+3,ii);
                }
} ini_reg(void)
{ outp(RB,0x16);      outp(RB+1,3);       outp(RB+2,0);
outp(RB+3,0);       outp(RB+4,0x36);outp(RB+5,0x02);
outp(RB+6,0);       outp(RB+7,0);       outp(RB+8,0x40);
outp(RB+9,0);       outp(RB+10,0);      outp(RB+11,0);

}
```

```
/* display a number at (x,y), size is (size_x X size_Y)     */ number_display(number,x,y,size_x,size_y,brightness)
int number,x,y,size_x,size_y,brightness;
{
int hx,hy,i,j,b;

b=brightness;          hx=size_x/2;          hy=size_y/2;

switch(number)
{
case 0:    line_show(x-hx,y-hy,x+hx,y-hy,b);
           line_show(x-hx,y-hy,x-hx,y+hy,b);
           line_show(x-hx,y+hy,x+hx,y+hy,b);
           line_show(x+hx,y-hy,x+hx,y+hy,b);
           break;

case 1: line_show(x,y-hy,x,y+hy,b);
        break;

case 2:    line_show(x-hx,y-hy,x+hx,y-hy,b);
           line_show(x+hy,y-hy,x+hx,y,b);
           line_show(x+hy,y,x-hx,y,b);
           line_show(x-hx,y,x-hx,y+hy,b);
           line_show(x-hx,y+hy,x+hx,y+hy,b);
           break;

case 3: line_show(x-hx,y-hy,x+hx,y-hy,b);
        line_show(x+hx,y-hy,x+hx,y+hy,b);
        line_show(x-hx,y,x+hx,y,b);
        line_show(x-hx,y+hy,x+hx,y+hy,b);
        break;

case 4: line_show(x-hx,y-hy,x-hx,y,b);
        line_show(x-hx,y,x+hx,y,b);
        line_show(x+hx,y-hy,x+hx,y+hy,b);
        break;

case 5:    line_show(x-hx,y-hy,x+hx,y-hy,b);
           line_show(x-hx,y-hy,x-hx,y,b);
           line_show(x-hx,y,x+hx,y,b);
           line_show(x+hx,y,x+hx,y+hy,b);
           line_show(x-hx,y+hy,x+hx,y+hy,b);
           break;

case 6:    line_show(x-hx,y-hy,x+hx,y-hy,b);
           line_show(x-hx,y-hy,x-hx,y+hy,b);
           line_show(x-hx,y,x+hx,y,b);
           line_show(x-hx,y+hy,x+hx,y+hy,b);
           line_show(x+hx,y,x+hx,y+hy,b);
           break;

case 7:    line_show(x-hx,y-hy,x+hx,y-hy,b);
           line_show(x+hx,y-hy,x+hx,y+hy,b);
           break;

case 8: line_show(x-hx,y-hy,x+hx,y-hy,b);
        line_show(x-hx,y,x+hx,y,b);
        line_show(x-hx,y+hy,x+hx,y+hy,b);
        line_show(x-hx,y-hy,x-hx,y+hy,b);
        line_show(x+hx,y-hy,x+hx,y+hy,b);
        break;

case 9:    line_show(x-hx,y-hy,x+hx,y-hy,b);
           line_show(x-hx,y,x+hx,y,b);
           line_show(x-hx,y+hy,x+hx,y+hy,b);
           line_show(x-hx,y-hy,x-hx,y,b);
           line_show(x+hx,y-hy,x+hx,y+hy,b);
           break;
```

```
}
} histogram_image(image,x,y,hist)
unsigned char huge *image;
int x,y;
long *hist;
{
int i,j,z;
long zzz;

for(i=0;i<256;i++)      *(hist+i)=0;
for(j=0;j<y;j++)
        for(i=0;i<x;i++)
            {
            zzz=j; zzz*=x; zzz+=i;
            z=*(image+zzz);
            *(hist+z)+=1;
            }
} show_hist_vertical(hist)
long *hist;
{
int i,ii,j,a,d;
float max,rate,g,gg;
double buf;

max=0; /* ii=0 */
for(i=0;i<256;i++)
        if(*(hist+i)>max)     {       max=*(hist+i);         /*        ii=i;*/        }
rate=34/max;  a=max;
/*
printf("max=%d, grey level=%d.\n",a,ii);
*/
line_show(566,0,566,470,255);
g=479;    g/=255;
for(i=0;i<256;i++)
        {
        buf=*(hist+i); buf*=rate;
        if(buf>0 && buf<2)   a=2;
        else                       a=buf;
        gg=i*g;  d=gg;
        line_show(566-a,d,567,d,255);
        }
}

/* get digits from a integer, nd is the number of the digits */ integer_to_digit(integer,nd,d)
int integer,nd,*d;
{
int i,n;

n=integer;

for(i=0;i<nd;i++)
        {
        n/=10;   n*=10;   *(d+i)=integer-n;   integer/=10;    n/=10;
        }
} equalized_grey_level_show(t1,t2)
int t1,t2;
{
int i,j,grey,d[3],t;
float g,dt;

dt=t2-t1;    dt/=8;
```

```
for(j=0;j<480;j++)
        {
        g=j;    g*=255;     g/=480;       grey=g;
        for(i=610;i<640;i++)
                {
                point_show(i,j,grey);
                }
        }
for(j=0;j<480;j++)
        for(i=532;i<610;i++) point_show(i,j,0);
line_show(567,0,567,480,255);
t=t1;
integer_to_digit(t,3,&d[0]);
number_display(d[2],578,6,7,9,255);
number_display(d[1],587,6,7,9,255);
number_display(d[0],596,6,7,9,255);

line_show(567,0,571,0,255);
                                                    line_show(606,0,609,0,255);

for(i=60;i<=420;i+=60)
{
j=i/60;
t=t1+j*dt;
integer_to_digit(t,3,&d[0]);
number_display(d[2],578,i,7,9,255);
number_display(d[1],587,i,7,9,255);
number_display(d[0],596,i,7,9,255);

line_show(567,i,571,i,255);
                                                    line_show(606,i,609,i,255);

}

/*
t=t1+2*dt;
integer_to_digit(t,3,&d[0]);
number_display(d[0],578,120,7,9,255);
number_display(d[1],587,120,7,9,255);
number_display(d[2],596,120,7,9,255);

line_show(567,120,571,120,255);
                                                    line_show(606,120,609,120,255);

t=t1+3*dt;
integer_to_
number_display(9,578,180,7,9,255);
number_display(5,587,180,7,9,255);

line_show(567,180,571,180,255);
                                                    line_show(606,180,609,180,255);

number_display(1,578,240,7,9,255);
number_display(2,587,240,7,9,255);
number_display(7,596,240,7,9,255);

line_show(567,240,571,240,255);
                                                    line_show(606,240,609,240,255);

number_display(1,578,300,7,9,255);
number_display(5,587,300,7,9,255);
number_display(9,596,300,7,9,255);

line_show(567,300,571,300,255);
                                                    line_show(606,300,609,300,255);

number_display(1,578,360,7,9,255);
number_display(9,587,360,7,9,255);
number_display(1,596,360,7,9,255);

line_show(567,360,571,360,255);
                                                    line_show(606,360,609,360,255);

number_display(2,578,420,7,9,255);
number_display(2,587,420,7,9,255);
number_display(3,596,420,7,9,255);

line_show(567,420,571,420,255);
                                                    line_show(606,420,609,420,255);

*/
t=t2;
integer_to_digit(t,3,&d[0]);
number_display(d[2],578,474,7,9,255);
number_display(d[1],587,474,7,9,255);
```

```
number_display(d[0],596,474,7,9,255);
                                        line_show(567,479,571,479,255);
                                        line_show(606,479,609,479,255);
}

/* the PSF is a image file */
/*          maximum neighbor: I=c2 [O(j) - c1 max(s1*O(j-1), s1*O(j+1))]    */
/*
            convolution:        I=H*O;
NO!         deconvolution:      O(n)=O(n-1)-a(I-O(n-1)*H);
*/
/* modified maxnb2.c, after convolution, the convolved image will be saved
into hard disk, the memory requirement can be reduced, the saved convolved
images will be named after original image with wild card '.cv1' and '.cv2' */ include "ypdef.h"
include <stdio.h>
include <alloc.h>
include <dos.h>
include <math.h> define XO 320
define YO 240

/*
void deconvolution(double huge *im, double huge *ob, int x, int y,
        double huge *h, int hx, int hy);
*/
void convolution(unsigned char huge *im, double huge *ob, int x, int y,
        double huge *h, int hx, int hy);
void matrix_sub(double huge *a, double huge *b, double huge *c, int x, int y);
void matrix_scale(double huge *a, int x, int y, float c);
void readdat_double(char datfile[30], double huge *c, long size);
void savedat_double(char datfile[30], double huge *c, long size);

void image_show_double(double huge *img, int sx, int sy, int x, int y);

main()
{
char cname[30],uname[30],lname[30],hname1[30],hname2[30],outname[30],
        convname1[30],convname2[30];
unsigned char huge *im1;
unsigned char huge *im2;
unsigned char huge *im3;
double huge *im;
double huge *h1;
double huge *h2;

double max1,max2,weight1,weight2;
float kx,ky,xb,yb,pp1,pp2,c1,c2;
unsigned int xx,yy;
int hx,hy,x,y,i,j,redo,pp,p1,p2;
char sv;
long zz,size;
unsigned char huge *psf1;
unsigned char huge *psf2;

printf("%lu bytes free in ram.\n",farcoreleft());
printf("center, upper, lower image names,: ");
scanf("%s %s %s",cname,uname,lname);          printf("\n");
printf("up/low PSF image name: ");
scanf("%s %s",hname1,hname2);                 printf("\n");

im1=(unsigned char huge *)read_image(uname,&x,&y);
image_show(im1,0,0,x,y);

psf1=(unsigned char huge *)read_image(hname1,&hx,&hy);
psf2=(unsigned char huge *)read_image(hname2,&hx,&hy);
```

```
size=x;           size*=y;

im=(double huge *)farcalloc(size,sizeof(double));

/*
ob=(double huge *)farcalloc(size,sizeof(double));
*/ size=hx;    size*=hy;
h1=(double huge *)farcalloc(size,sizeof(double));
h2=(double huge *)farcalloc(size,sizeof(double));
for(zz=0;zz<size;zz++)
        {           *(h1+zz)=*(psf1+zz);  *(h2+zz)=*(psf2+zz); }
weight1=weight2=0;
for(zz=0;zz<size;zz++)
        {
        if(*(h1+zz)<0)        *(h1+zz)*=-1;
        if(*(h2+zz)<0)        *(h2+zz)*=-1;
        weight1+=*(h1+zz);
        weight2+=*(h2+zz);
        }
printf("\nweight=%lf.\n",weight1);
for(zz=0;zz<size;zz++)
        {
        *(h1+zz)/=weight1;    *(h2+zz)/=weight2;
        printf("%lf ",*(h1+zz));
        }
/*
if( im==NULL || ob==NULL)
        {
        printf("no enough memory.\n");
        exit();
        }
else
        printf("%lu bytes allocated.\n",size);
*/ printf("\n");
for(j=0;j<y;j++)
        for(i=0;i<x;i++)
                {
                zz=j;    zz*=x;    zz+=i;
                *(im+zz)=*(im1+zz);
                }
convolution(im1,im,x,y,h1,hx,hy);
/*
image_show_double(im,0,y,x,y);
*/
strcpy(convname1,uname);       strcat(convname1,".cv1");
save_image(convname1,XO-x/2,YO-y/2,XO-x/2+x-1,YO-y/2+y-1);
im2=(unsigned char huge *)read_image(lname,&x,&y);

image_show(im2,x,0,x,y);
for(j=0;j<y;j++)
        for(i=0;i<x;i++)
                {
                zz=j;    zz*=x;    zz+=i;
                *(im+zz)=*(im2+zz);
                }
convolution(im2,im,x,y,h2,hx,hy);

strcpy(convname2,lname);       strcat(convname2,".cv2");
save_image(convname2,XO-x/2,YO-y/2,XO-x/2+x-1,YO-y/2+y-1);
farfree((double far *)im);
im3=(unsigned char huge *)read_image(cname,&x,&y);
image_show(im3,2*x,0,x,y);

do{
printf("\ninput c1, c2: ");    scanf("%f %f",&c1,&c2);         printf("\n");
```

```
for(j=0;j<y;j++)
        for(i=0;i<x;i++)
                {
                    zz=j;       zz*=x;      zz+=i;
                    p1=*(im1+zz);           p2=*(im2+zz);
                    pp1=(p1>p2)? p1:p2;  pp1*=c1;
                    pp2=*(im3+zz);
                    pp2-=pp1; pp2*=c2;
                    if(pp2<0) pp2=0;
                    if(pp2>255)             pp2=255;
                    pp=pp2;
                    point_show(XO-x/2+i,YO-y/2+j,pp);
                }
printf("OK?(y) ");
}while(getche()!='y');

printf("\nsave image?(y) ");
if(getche()=='y')
        {
            printf("\noutput image name: ");
            scanf("%s",outname);  printf("\n");
            save_image(outname,XO-x/2,YO-y/2,XO-x/2+x-1,YO-y/2+y-1);
        }
printf("\n");
}

/*
        deconvolution:
                O(n)= O(n-1)-a(I-O(n-1)*H);

void deconvolution(double huge *im, double huge *ob, int x, int y,
        double huge *h, int hx, int hy)
{
int i,j,p,k1,k2;
long zz,z;
double huge *c;

zz=x;   zz*=y;
c=(double huge *)farcalloc(zz,sizeof(double));

for(j=0;j<y;j++)
        for(i=0;i<x;i++)
                {
                    zz=j;   zz*=x;  zz+=i;
                    *(ob+zz)=*(im+zz);
                }
for(i=0;i<1;i++)
        {
            printf("\n---%d\n",i);
            convolution(c,ob,x,y,h,hx,hy);
            image_show_double(c,0,0,x,y);
            matrix_sub(im,c,c,x,y);
            image_show_double(c,x+10,0,x,y);
            matrix_scale(c,x,y,1.2);
            matrix_sub(ob,c,ob,x,y);
            matrix_scale(ob,x,y,0.9);
            image_show_double(ob,2*(x+10),0,x,y);
        }
farfree((double far *)c);

}

*/
/*
        convolution:    IM=OB*H;

IM and OB have the same dimension (x,y),
                        H's dimension is (hx,hy), if hx or hy is even
                        number, it will be minus 1.
```

*/

```c
void convolution(unsigned char huge *img, double huge *ob, int x, int y,
        double huge *h, int hx, int hy)
{
int hhx,hhy,i,j,k1,k2,yy,p;
double c,c1,c2;
long z1;

hhx=(hx-1)/2;      hhy=(hy-1)/2;
z1=hhy;   z1*=hx;   z1+=hhx;
h+=z1;

if(y>36)   yy=y/3;
else            yy=y;
for(i=0;i<yy;i++)      printf("_"); printf("\r");
for(j=0;j<y;j++)
        {
        if(y==yy)  printf("+");
        else              if(j==(j/3)*3)      printf("+");
        for(i=0;i<x;i++)
                {
                z1=j;     z1*=x;    z1+=i;
                c=0;
                for(k2=-hhy;k2<=hhy;k2++)
                        for(k1=-hhx;k1<=hhx;k1++)
                              if((j+k2)>=0 && (j+k2)<y && (i+k1)>=0 && (i+k1)<x)
                                    {
                                    c1=*(ob+z1+k2*x+k1);
                                    c2=*(h+k2*hx+k1);
                                    c+=(c1*c2);
                                    }
                p=c;
                *(img+z1)=p;
                point_show(XO-x/2+i,YO-y/2+j,p);
                }
        }
} void matrix_sub(double huge *a, double huge *b, double huge *c, int x, int y)
{
int i,j;

for(j=0;j<y;j++)
        for(i=0;i<x;i++)
                {
                *c=*a-*b;  a++;     b++;     c++;
                }
} void matrix_scale(double huge *a, int x, int y, float c)
{
int i,j;

for(j=0;j<y;j++)
        for (i=0;i<x;i++)
                {          (*a)*=c;   a++;      }
} define SPEC_RANG 16 void savedat_double(char datfile[30], double huge *c, long size)
{
FILE *fp;
double *buf;
int fnum,bufsize,i,j;
char fname[30],s0[30];

bufsize=SPEC_RANG*16;
```

```
fnum=size/bufsize;
if(NULL==(buf=(double *)calloc(bufsize,sizeof(double))))
        {
        printf("no enough memory, exit.\n");          exit(1);
        }
for(i=0;i<fnum;i++)
        {
        for(j=0;j<bufsize;j++)
                {
                *(buf+j)=*c;                           c++;
                }
        itoa(i,s0,10);
        strcpy(fname,datfile);
        strcat(fname,s0);
        if((fp=fopen(fname,"wb"))==NULL)
                {
                printf("data file open failure.\n");
                exit(1);
                }
        fwrite((double *)buf,sizeof(double),bufsize,fp);
        fclose(fp);
        }
free((double *)buf);
} void readdat_double(char datfile[30], double huge *c, long size)
{
FILE *fp;
double *buf;
int fnum,bufsize,i,j;
char fname[30],s0[30];

bufsize=SPEC_RANG*16;
fnum=size/bufsize;
if(NULL==(buf=(double *)calloc(bufsize,sizeof(double))))
        {
        printf("no enough memory, exit.\n");          exit(1);
        }
for(i=0;i<fnum;i++)
        {
        itoa(i,s0,10);
        strcpy(fname,datfile);
        strcat(fname,s0);
        if((fp=fopen(fname,"rb"))==NULL)
                {
                printf("data file open failure.\n");
                exit(1);
                }
        fread((double *)buf,sizeof(double),bufsize,fp);
        fclose(fp);
        for(j=0;j<bufsize;j++)
                {       *c=*(buf+j);                   c++;
                }
        }
free((double *)buf);

} void image_show_double(double huge *img, int sx, int sy, int x, int y)
{
int k1,k2,p;
long zz;

for(k2=0;k2<y;k2++)
        for(k1=0;k1<x;k1++)
                {
                zz=k2;   zz*=x;   zz+=k1;
                p=*(img+zz);      if(p<0)   p=-p;    if(p>255) p=255;
                point_show(sx+k1,sy+k2,p);
```

```
              }
}

/*............. image division, can save results as float number ............*/ include "ypdef.h"
include <stdio.h>
include <dos.h>
include <alloc.h>
define BASEMEM 0xD000
define CONREG 0x300 main ()
{
char imgname1[50],imgname2[50],outname[50],ffile[50];
unsigned char huge *image;
unsigned char huge *board;
unsigned char huge *p;
int choice,c,i,j,x,y,ws,wrongname,pp,ppp;
long size,zz;
int n;
float s,p1,p2,p3;
FILE *fp;
/* read an image from disk into memory */ printf("%lu bytes free in ram.\n",farcoreleft());
printf("div.=(image1/image2)*scale_factor.\n");

printf("the names of image1, image2, scale_factor: ");
scanf("%s %s %f",imgname1,imgname2,&s);         printf("\n");
printf("do you want to save division results as float number:(y) ");
if(getche()=='y')
        {
        printf("\nfloat data file name: ");
        scanf("%s",ffile);      printf("\n");
        }
fp=fopen(ffile,"wb");

image=(unsigned char huge *)read_image(imgname1,&x,&y);
printf("display image1.\n");
image_show(image,0,0,x,y);
farfree((unsigned char far *)image);
p=(unsigned char huge *)farcalloc(1,1);
image=(unsigned char huge *)read_image(imgname2,&x,&y);
for(j=0;j<y;j++)
        for(i=0;i<x;i++)
                {
                zz=j;    zz*=x;    zz+=i;
                get_point_value(i,j,p);  pp=*p;    p1=pp;
                ppp=*(image+zz);                   p2=ppp;
                p3=(p1/p2);
                fwrite(&p3,sizeof(float),1,fp);
                p3*=s;   pp=p3;
                if(pp>255) pp=255;
                point_show(i,j,pp);
                }
fclose(fp);
printf("save image?(y): ");
if(getche()=='y')
        {
        printf("\noutput image name: ");
        scanf("%s",outname);    printf("\n");
        save_image_screen(outname,0,0,x-1,y-1);
        }
} save_image_screen(imname,x1,y1,x2,y2)
char imname[50];
int x1,y1,x2,y2;
```

```c
{
int wrongname,i,j,x,y,k,start_line,end_line,start_blc,end_blc,
        start_y_offset,end_y_offset;
unsigned char huge *mem;
unsigned char huge *mem_keep;
unsigned char ini_stat,stat;
unsigned char p;
long zz;
FILE *fp;
char ix[8],iy[8];

do{
wrongname=0;
if((fp=fopen(imname,"wb"))==NULL)
        {
        wrongname=1;
        printf("wrong name! try again: ");
        scanf("%s",imname);   printf("\n");
        }
}while(wrongname==1);
mem=(unsigned char huge *)MK_FP(BASEMEM,0);
x=x2-x1+1;      y=y2-y1+1;
itoa(x,ix,10);          itoa(y,iy,10);
for(i=0;i<8;i++)        fputc(ix[i],fp);
for(i=0;i<8;i++)        fputc(iy[i],fp);

start_blc=y1/64;            end_blc=(y2+1)/64;
start_y_offset=y1%64;       end_y_offset=(y2+1)%64;
mem_keep=mem+x1;
zz=start_y_offset;   zz*=1024;    zz+=x1;
mem +=zz;

ini_stat=0x16;
        for(i=start_blc;i<=end_blc;i++)
                {
                stat=(i<<5)&0xe0;
                stat |=ini_stat;
                outp(CONREG,stat);

if(i==start_blc)       start_line=start_y_offset;
                        else       start_line=0;
                if(i==end_blc) end_line=end_y_offset;
                        else       end_line=64;
                for(j=start_line;j<end_line;j++)
                        {
                        for(k=0;k<x;k++)
                                {
                                p=*mem;       fputc(p,fp);
                                mem++;
                                }
                        mem+=(1024-x);
                        }
                mem=mem_keep;

}
printf("----- a %d X %d image %s is saved.\n",x,y,imname);
} include <stdio.h>
include <alloc.h>
include <dos.h> define BP 0x3F8        /* for com1. baseport register address*/
define CONREG 0x300    /* pcplus regster base address */ unsigned char huge *read_image(char imname[30], int *x, int *y);
void image_show(unsigned char huge *im_ad, int sx, int sy, int x, int y);

main()
```

```
{
int x,y,sx,sy;
char imname[30];
unsigned char huge *mem;

printf("%lu bytes free.\n",farcoreleft());
        printf("input image file name, upper-left corner (sx,sy):");
        scanf("%s %d %d",imname,&sx,&sy);                    printf("\n");
        mem=(unsigned char huge *)read_image(imname,&x,&y);
        image_show(mem,sx,sy,x,y);
        printf("\n");

}
```

I claim:

1. A method of measuring an oxygen concentration or partial pressure of a fluid comprising the steps of:
   (a) contacting the fluid with a sensor comprising a housing containing a lipid soluble fluorescent probe substance having a fluorescence lifetime ($\tau$) which is sensitive to quenching by oxygen, admixed in a nonpolar solvent;
   (b) irradiating the fluorescent probe substance of step (a) within the sensor housing with continuous, linearly polarized ultraviolet light at wavelengths strongly absorbed by the fluorescent probe substance to emit fluorescence having vector components parallel and perpendicular to the plane of polarization of the ultraviolet light;
   (c) resolving the emitted fluorescence of step (b) into vector components parallel and perpendicular to the plane of polarization of the ultraviolet light;
   (d) calculating a fluorescence anisotropy in time of the fluorescence emitted by the fluorescent probe substance of step (a) within the sensor housing from the vector components of step (c) by applying a first mathematical function, the first mathematical function being in the form of a first equation; and
   (e) applying a second mathematical function which relates fluorescence anisotropy to oxygen concentration or partial pressure, the second mathematical function being in the form of a second equation.

2. The method of claim 1 wherein the fluorescence lifetime ($\tau$) is related to oxygen concentration or oxygen partial pressure by the following equation:

$$\tau = \frac{\tau_o}{1 + K_D} \text{ or } \frac{\tau_o}{1 + \alpha K_D PO_2}$$

wherein $\alpha$ is a Bunsen solubility coefficient, $K_D$ is a dynamic quench constant, $\tau_o$ is a fluorescence lifetime in the absence of $O_2$ is oxygen concentration, and $PO_2$ is oxygen partial pressure.

3. The method of claim 1 wherein fluorescence anisotropy is related to oxygen partial pressure by the following equation:

$$PO_2 = \frac{A_0 - A(6\bar{R}\tau_o + 1)}{\alpha K_D (A - A_0)}$$

wherein A is fluorescence anisotropy, defined as $$A = \frac{I_\| G - I_\perp}{I_\| G + 2I_\perp}$$

wherein $I_\|$ and $I_{195}$ are intensities of fluorescence emission having electric vectors respectively parallel and perpendicular to that of the linearly polarized ultraviolet light of step (b), G is an empirical correction factor used to correct for transmission efficiency in parallel and perpendicular planes, R is mean molecular rotation time in radians/sec, $A_0$ is fluorescence anisotropy in a "frozen" state, in the absence of Brownian rotation, $\alpha$ is a Bunsen solubility coefficient, $K_D$ is a dynamic quench constant, and $\tau_o$ is a fluorescence lifetime in the absence of $O_2$.

4. The method of claims 1 or 3 additionally comprising the step of selecting a fluorescence anisotropy of the lipid soluble fluorescent probe substance to be less than about 0.4.

5. The method of claim 1 additionally comprising the step of selecting the lipid soluble fluorescent probe substance to be pyrene.

6. The method of claim 5 additionally comprising the step of selecting a fluorescence lifetime of the $O_2$-quenchable fluorescent substance to be in the range of 40 to 1400 nanoseconds.

7. The method of claim 1 additionally comprising the step of selecting the lipid soluble fluorescent probe substance to be pyrene-butyric acid or a salt form thereof.

8. The method of any one of claims 1, 5 or 7 additionally comprising the step of selecting the nonpolar solvent to be paraffin or mineral oils.

9. The method of any one of claims 1, 5 or 7 additionally comprising the step of irradiating the fluorescent probe substance of the sensor with linearly polarized ultraviolet light by selecting the linearly polarized ultraviolet light to be transmitted by a single mode polarization-preserving glass fiber.

10. The method of any one of claims 1, 3, 5 or 7 additionally comprising the step of selecting the sensor to comprise a tip and a thermistor to correct anisotropy measurements for sensor tip temperature according to the following equation:

$$\frac{A_0}{A} = \frac{1 + R_g T}{\eta V} \tau$$

wherein $R_g$ a gas constant, T is temperature, $\eta$ is viscosity, V is hydrodynamic volume of a fluorophore, A is fluorescence anisotropy, $A_0$ is a fluorescence anisotropy in a "frozen" state, in the absence of Brownian rotation, and $\tau$ is a fluorescence lifetime of a fluorophore.

11. The method of any one of claims 1, 5 or 7, additionally composing the step of sealing the sensor from the fluid by an $O_2$-permeable membrane which is impermeable to the nonpolar solvent within the sensor housing.

12. The method of claim 7 additionally comprising the step of selecting a fluorescence lifetime of the $O_2$-quenchable fluorescent substance to be in the range of 35 to 135 nanoseconds.

13. The method of claim 1 additionally comprising the step of selecting the $O_2$-permeable membrane to be polyethylene.

14. The method of claim 1 additionally comprising the step of exposing the fluorescent probe substance of the sensor to the linearly polarized ultraviolet light of step (b), wherein the method additionally comprises selecting the linearly polarized ultraviolet light to have a wavelength less than about 400 nm.

15. The method of claim 1 additionally comprising the step of selecting the sensor to comprise multiple sensors formed from a bundle of single mode polarization-preserving glass fibers to permit a determination of spatial distribution of $PO_2$ of a surface.

* * * * *

UNITED STATES PATENT AND TRADEMARK OFFICE
CERTIFICATE OF CORRECTION

PATENT NO. : 5,495,850
DATED : March 5, 1996
INVENTOR(S) : Ralph Zuckerman

It is certified that error appears in the above-identified patent and that said Letters Patent is hereby corrected as shown below:

| | DELETE | INSERT |
|---|---|---|
| item [56] Title page, col. 2, l. 1 | "porscence", J. Biol., Chem. 262(12);" | --phorescence", J. Biol. Chem., 262(12):-- |
| col. 3, l. 43 | "onds ($10^{-9}$ sec), and ..." | --onds ($10^{-9}$ sec), and ...-- |
| col. 6, eq. 1 | "$A(t) = A_o e^{-6Rt}$" | --$A(t) = A_o e^{-6\bar{R}t}$-- |
| col. 6, l. 6 | "after pulsed excitation, R is mean ..." | --after pulsed excitation, $\bar{R}$ is mean ...- |
| col. 7, l. 27 | "... a hugh number of " | --... a huge number of -- |
| col. 7, eq. 7 | "$= \dfrac{A_o(\alpha K_d PO_2 + 1)}{6\bar{R}\tau_o + \alpha K_D PO_2 + 1}$" | --$= \dfrac{A_o(\alpha K_D PO_2 + 1)}{6\bar{R}\tau_o + \alpha K_D PO_2 + 1}$-- |
| col. 7, l. 62 | " where $I_{81}$ and $I_{193}$ are the ... " | -- where $I_{\parallel}$ and $I_{\perp}$ are the ... -- |
| col. 8, l. 8 | " ... illuminated with linearly " | -- ... illuminated with continuous -- |
| col. 8, l. 9 | " polarized ultraviolet light (UV) by ..." | -- visible light by ... -- |
| col. 8, l. 25 | " vector components ($I_{\parallel}$ and $I_{\perp}$ are ... " | -- vector components ($I_{\parallel}$ and $I_{\perp}$) are . |
| col. 10, l. 46 | " components ($I_{\parallel}$ and $I_{\perp}$ are ... " | -- components ($I_{\parallel}$ and $I_{\perp}$) are ... -- |
| col. 11, l. 21 | "... passed through a Clan- " | -- ... passed through a Glan- -- |

UNITED STATES PATENT AND TRADEMARK OFFICE
CERTIFICATE OF CORRECTION

PATENT NO. : 5,495,850
DATED : March 5, 1996
INVENTOR(S) : Ralph Zuckerman

It is certified that error appears in the above-identified patent and that said Letters Patent is hereby corrected as shown below:

| DELETE | INSERT |
|---|---|
| col. 11, l. 34 " nents ($I_\|$ and $I_\perp$ were ... " | -- nents ($I_\|$ and $I_\perp$) were ... -- |
| col. 75, l. 34 " $\tau = \dfrac{\tau_o}{1 + K_D}$ " | -- $\tau = \dfrac{\tau_o}{1 + K_D[O_2]}$ -- |
| col. 75, l. 36 " wherein $\propto$ is ... " | -- wherein $\alpha$ is ... -- |
| col. 75, l. 38 " absence of $O_2$ is oxygen ... " | -- absence of $O_2$, $[O_2]$ is oxygen ... -- |
| col. 75, l. 52 " wherein $I_\|$ and $I_{195}$ are ... " | -- wherein $I_\|$ and $I_\perp$ are ... -- |
| col. 75, l. 57 "R is mean ... " | -- $\bar{R}$ is mean ... -- |
| col. 75, l. 59 "Brownian rotation, $\propto$ is a ... " | -- Brownian rotation, $\alpha$ is a ... -- |

Signed and Sealed this

Sixth Day of May, 1997

Attest:

BRUCE LEHMAN

*Attesting Officer*    *Commissioner of Patents and Trademarks*